United States Patent
Weber et al.

(10) Patent No.: US 9,073,930 B2
(45) Date of Patent: Jul. 7, 2015

(54) DIPEPTIDYL PEPTIDASE-IV INHIBITORS FOR THE TREATMENT OR PREVENTION OF DIABETES

(71) Applicant: Merck Sharp & Dohme Corp., Rahway, NJ (US)

(72) Inventors: Ann E. Weber, Scotch Plains, NJ (US); Tesfaye Biftu, Freehold, NJ (US)

(73) Assignee: Merck Sharp & Dohme, Rahway, NJ (US)

( * ) Notice: Subject to any disclaimer, the term of this patent is extended or adjusted under 35 U.S.C. 154(b) by 0 days.

(21) Appl. No.: 14/376,787

(22) PCT Filed: Feb. 12, 2013

(86) PCT No.: PCT/US2013/025714
§ 371 (c)(1),
(2) Date: Aug. 5, 2014

(87) PCT Pub. No.: WO2013/122920
PCT Pub. Date: Aug. 22, 2013

(65) Prior Publication Data
US 2015/0011590 A1    Jan. 8, 2015

Related U.S. Application Data

(60) Provisional application No. 61/600,196, filed on Feb. 17, 2012, provisional application No. 61/672,821, filed on Jul. 18, 2012.

(51) Int. Cl.
*A61K 31/4439* (2006.01)
*A61K 31/4162* (2006.01)
*C07D 487/04* (2006.01)
*A61K 45/06* (2006.01)
*A61K 31/155* (2006.01)

(52) U.S. Cl.
CPC .............. *C07D 487/04* (2013.01); *A61K 45/06* (2013.01); *A61K 31/155* (2013.01); *A61K 31/4162* (2013.01); *A61K 31/4439* (2013.01)

(58) Field of Classification Search
USPC ........................................ 514/407; 548/360.5
See application file for complete search history.

(56) References Cited

U.S. PATENT DOCUMENTS

| | | | |
|---|---|---|---|
| 7,750,034 B2 * | 7/2010 | Biftu et al. | 514/406 |
| 8,653,059 B2 * | 2/2014 | Biftu et al. | 514/183 |
| 8,853,212 B2 * | 10/2014 | Wilkening et al. | 514/249 |
| 2009/0270467 A1 | 10/2009 | Biftu et al. | |
| 2010/0120863 A1 | 5/2010 | Biftu et al. | |
| 2013/0203786 A1 * | 8/2013 | Hicks et al. | 514/264.1 |

FOREIGN PATENT DOCUMENTS

| | | |
|---|---|---|
| WO | WO02076450 A1 | 10/2002 |
| WO | WO03000180 A2 | 1/2003 |
| WO | WO03000181 A2 | 1/2003 |
| WO | WO03004498 A1 | 1/2003 |
| WO | WO03082817 A2 | 10/2003 |
| WO | WO2004007468 A1 | 1/2004 |
| WO | WO2004032836 A2 | 4/2004 |
| WO | WO2004037169 A2 | 5/2004 |
| WO | WO2004043940 A1 | 5/2004 |
| WO | WO2004050022 A2 | 6/2004 |
| WO | WO2004058266 A1 | 7/2004 |
| WO | WO2004064778 A2 | 8/2004 |
| WO | WO2004069162 A2 | 8/2004 |
| WO | WO2004103276 A2 | 12/2004 |
| WO | WO2004110436 A1 | 12/2004 |
| WO | WO2004112701 A2 | 12/2004 |
| WO | WO2005011581 A2 | 2/2005 |
| WO | WO2005044195 A2 | 5/2005 |
| WO | WO2005108382 A1 | 11/2005 |

(Continued)

OTHER PUBLICATIONS

Dorwald; "Side Reactions in Organic Synthesis: A Guide to Successful Synthesis Design" 2005 Wiley-VCH Verlag GmbH & Co. KGaA, Wienheim.*
Biftu; Bioorganic and Medicinal Chemistry Letters 2007, 17, 3384-3387.*
Silverman;The Organic Chemistry of Drug Design and Drug Action, 2nd Ed, 2004, Elsevier, pp. 29 to 34.*

*Primary Examiner* — John Mabry
*Assistant Examiner* — Daniel Carcanague
(74) *Attorney, Agent, or Firm* — Janet E. Fair; Catherine D. Fitch

(57) ABSTRACT

The present invention is directed to novel substituted dihydropyrrolopyrazoles of structural Formula I which are inhibitors of the dipeptidyl peptidase-IV enzyme and which are useful in the treatment or prevention of diseases in which the dipeptidyl peptidase-IV enzyme is involved, such as diabetes and particularly Type 2 diabetes. The invention is also directed to pharmaceutical compositions comprising these compounds and the use of these compounds and compositions in the prevention or treatment of such diseases in which the dipeptidyl peptidase-IV enzyme is involved.

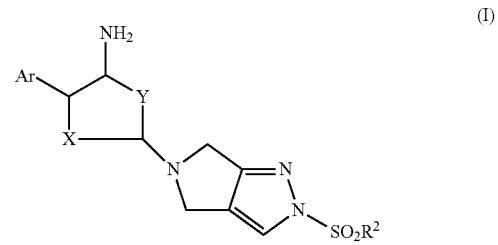

(I)

15 Claims, No Drawings

(56) References Cited

FOREIGN PATENT DOCUMENTS

| | | |
|---|---|---|
| WO | WO2005116029 A1 | 12/2005 |
| WO | WO2006009886 A1 | 1/2006 |
| WO | WO2006023750 A2 | 3/2006 |
| WO | WO2006039325 A2 | 4/2006 |
| WO | WO2006065826 A2 | 6/2006 |
| WO | WO2006078676 A2 | 7/2006 |
| WO | WO2006104997 A2 | 10/2006 |
| WO | WO2006119260 A2 | 11/2006 |
| WO | WO2006127530 A2 | 11/2006 |
| WO | WO2007024993 A2 | 3/2007 |
| WO | WO2007035198 A2 | 3/2007 |
| WO | WO2007070434 A2 | 6/2007 |
| WO | WO2007078726 A2 | 7/2007 |
| WO | WO2007087231 A2 | 8/2007 |
| WO | WO2007097931 A2 | 8/2007 |
| WO | WO2007126745 A2 | 11/2007 |
| WO | WO2007136603 A2 | 11/2007 |
| WO | WO2008060488 A1 | 5/2008 |
| WO | WO2009025784 A1 | 2/2009 |
| WO | WO2010056708 A1 | 5/2010 |
| WO | WO2011028455 A1 | 3/2011 |
| WO | WO2011037793 A1 | 3/2011 |
| WO | WO 2011103256 * | 8/2011 |
| WO | WO2011146358 A1 | 11/2011 |
| WO | WO2012078448 | 6/2012 |
| WO | WO2012118945 | 9/2012 |
| WO | WO2013003249 A1 | 1/2013 |
| WO | WO2013003250 A1 | 1/2013 |
| WO | WO2013006526 A2 | 1/2013 |

* cited by examiner

DIPEPTIDYL PEPTIDASE-IV INHIBITORS FOR THE TREATMENT OR PREVENTION OF DIABETES

CROSS-REFERENCE TO RELATED APPLICATIONS

This application is a U.S. National Phase application under 35 U.S.C. §371 of PCT Application No. PCT/US2013/025714, filed Feb. 12, 2013, which published as WO 2013/122920 A1 on Aug. 22, 2013, and claims priority under 35 U.S.C. §365(b) from United States provisional patent application Nos. 61/672,821, filed Jul. 18, 2012, and 61/600,196, filed Feb. 17, 2012.

FIELD OF THE INVENTION

The present invention relates to substituted dihydropyrrolopyrazoles which are inhibitors of the dipeptidyl peptidase-IV enzyme ("DPP-4 inhibitors") and which are useful in the treatment or prevention of diseases in which the dipeptidyl peptidase-IV enzyme is involved, such as diabetes and particularly Type 2 diabetes. The invention is also directed to pharmaceutical compositions comprising these compounds and the use of these compounds and compositions in the prevention or treatment of such diseases in which the dipeptidyl peptidase-IV enzyme is involved.

BACKGROUND OF THE INVENTION

Diabetes refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type 2 diabetes mellitus are at especially increased risk of macrovascular and microvascular complications, including coronary heart disease, stroke, peripheral vascular disease, hypertension, nephropathy, neuropathy, and retinopathy. Therefore, therapeutical control of glucose homeostasis, lipid metabolism and hypertension are critically important in the clinical management and treatment of diabetes mellitus.

There are two generally recognized forms of diabetes. In Type 1 diabetes, or insulin-dependent diabetes mellitus (IDDM), patients produce little or no insulin, the hormone which regulates glucose utilization. In Type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

Compounds that are inhibitors of the dipeptidyl peptidase-IV ("DPP-4") enzyme have also been found useful for the treatment of diabetes, particularly Type 2 diabetes [See WO 97/40832; WO 98/19998; U.S. Pat. Nos. 5,939,560; 6,303,661; 6,699,871; 6,166,063; Bioorg. Med. Chem. Lett., 6: 1163-1166 (1996); Bioorg. Med. Chem. Lett., 6: 2745-2748 (1996); D. J. Drucker in Exp. Opin. Invest. Drugs, 12: 87-100 (2003); K. Augustyns, et al., Exp. Opin. Ther. Patents, 13: 499-510 (2003); Ann E. Weber, J. Med. Chem., 47: 4135-4141 (2004); J. J. Hoist, Exp. Opin. Emerg. Drugs, 9: 155-166 (2004); D. Kim, et al., J. Med. Chem., 48: 141-151 (2005); K. Augustyns, Exp. Opin. Ther. Patents, 15: 1387-1407 (2005); H.-U. Demuth in Biochim. Biophys. Acta, 1751: 33-44 (2005); and R. Mentlein, Exp. Opin. Invest. Drugs, 14: 57-64 (2005).

Additional patent publications that disclose DPP-4 inhibitors useful for the treatment of diabetes are the following: WO 2006/009886 (26 Jan. 2006); WO 2006/039325 (13 Apr. 2006); WO 2006/058064 (1 Jun. 2006); WO 2006/127530 (30 Nov. 2006); WO 2007/024993 (1 Mar. 2007); WO 2007/070434 (21 Jun. 2007); WO 2007/087231 (2 Aug. 2007); WO 07/097,931 (30 Aug. 2007); WO 07/126,745 (8 Nov. 2007); WO 07/136,603 (29 Nov. 2007); WO 08/060,488 (22 May 2008); WO2009025784; WO2010056708; WO2011037793; WO2011028455 and WO2011146358.

The usefulness of DPP-4 inhibitors in the treatment of Type 2 diabetes is based on the fact that DPP-4 in vivo readily inactivates glucagon like peptide-1 (GLP-1) and gastric inhibitory peptide (GIP). GLP-1 and GIP are incretins and are produced when food is consumed. The incretins stimulate production of insulin. Inhibition of DPP-4 leads to decreased inactivation of the incretins, and this in turn results in increased effectiveness of the incretins in stimulating production of insulin by the pancreas. DPP-4 inhibition therefore results in an increased level of serum insulin. Advantageously, since the incretins are produced by the body only when food is consumed, DPP-4 inhibition is not expected to increase the level of insulin at inappropriate times, such as between meals, which can lead to excessively low blood sugar (hypoglycemia). Inhibition of DPP-4 is therefore expected to increase insulin without increasing the risk of hypoglycemia, which is a dangerous side effect associated with the use of insulin secretagogues.

DPP-4 inhibitors also have other therapeutic utilities, as discussed herein. New compounds are needed so that improved DPP-4 inhibitors can be found for the treatment of diabetes and potentially other diseases and conditions. In particular, there is a need for DPP-4 inhibitors that are selective over other members of the family of serine peptidases that includes quiescent cell proline dipeptidase (QPP), DPP8, and DPP9 [see G. Lankas, et al., "Dipeptidyl Peptidase-IV Inhibition for the Treatment of Type 2 Diabetes: Potential Importance of Selectivity Over Dipeptidyl Peptidases 8 and 9," Diabetes, 54: 2988-2994 (2005); N. S. Kang, et al., "Docking-based 3D-QSAR study for selectivity of DPP4, DPP8, and DPP9 inhibitors," Bioorg. Med. Chem. Lett., 17: 3716-3721 (2007)].

The therapeutic potential of DPP-4 inhibitors for the treatment of Type 2 diabetes is discussed by (i) D. J. Drucker, Exp. Opin. Invest. Drugs, 12: 87-100 (2003); (ii) K. Augustyns, et al., Exp. Opin. Ther. Patents, 13: 499-510 (2003); (iii) J. J. Hoist, Exp. Opin. Emerg. Drugs, 9: 155-166 (2004); (iv) H.-U. Demuth, et al., Biochim Biophys. Acta, 1751: 33-44 (2005); (v) R. Mentlein, Exp. Opin. Invest. Drugs, 14: 57-64 (2005); (vi) K. Augustyns, "Inhibitors of proline-specific dipeptidyl peptidases: DPP IV inhibitors as a novel approach for the treatment of Type 2 diabetes," Exp. Opin. Ther. Patents, 15: 1387-1407 (2005); (vii) D. J. Drucker and M. A. Nauck, "The incretin system: GLP-1 receptor agonists and dipeptidyl peptidase-4 inhibitors in Type 2 diabetes," The Lancet, 368: 1696-1705 (2006); (viii) T. W. von Geldern and J. M. Trevillyan, ""The Next Big Thing" in Diabetes: Clinical Progress on DPP-IV Inhibitors," Drug Dev. Res., 67: 627-642 (2006); (ix) B. D. Green et al., "Inhibition of dipeptidyl peptidase IV activity as a therapy of Type 2 diabetes," *Exp. Opin. Emerging Drugs*, 11: 525-539 (2006); (x) J. J. Holst and C. F. Deacon, "New Horizons in Diabetes Therapy," *Immun., Endoc. & Metab. Agents in Med. Chem.*, 7: 49-55 (2007); (xi) R. K. Campbell, "Rationale for Dipeptidyl Peptidase 4 Inhibitors: a New Class of Oral Agents for the Treatment of Type 2 Diabetes Mellitus," *Ann. Pharmacother.*, 41: 51-60 (2007); (xii) Z. Pei, "From the bench to the bedside: Dipeptidyl peptidase IV inhibitors, a new class of oral antihyperglycemic agents," *Curr. Opin. Drug Discovery Development*, 11: 512-532 (2008); and (xiii) J. J. Hoist, et al., "Glucagon-like peptide-1, glucose homeostasis, and diabetes, *Trends in Molecular Medicine*, 14: 161-168 (2008). Specific DPP-4 inhibitors either already approved or under clinical investigation for the treatment of Type 2 diabetes include sitagliptin, vildagliptin, saxagliptin, alogliptin, carmegliptin, melogliptin, and dutogliptin.

SUMMARY OF THE INVENTION

The present invention is directed to substituted dihydropyrrolopyrazoles which are inhibitors of the dipeptidyl peptidase-IV enzyme ("DPP-4 inhibitors") and which are useful in the treatment or prevention of diseases in which the dipeptidyl peptidase-IV enzyme is involved, such as diabetes and particularly Type 2 diabetes. The invention is also directed to pharmaceutical compositions comprising these compounds and the use of these compounds and compositions in the prevention or treatment of such diseases in which the dipeptidyl peptidase-IV enzyme is involved.

DETAILED DESCRIPTION OF THE INVENTION

The present invention relates to substituted dihydropyrrolopyrazoles that are useful as inhibitors of dipeptidyl peptidase-IV. Compounds of the present invention are described by structural Formula I:

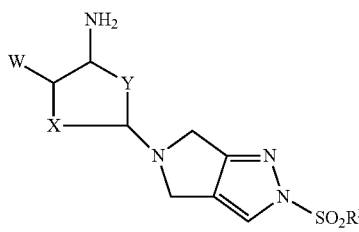

(I)

or a pharmaceutically acceptable salt thereof; wherein
W is selected from the group consisting of phenyl, napthyl, heteroaryl and non-aromatic heterocyclyl wherein the phenyl, napthyl, heteroaryl and non-aromatic heterocyclyl are unsubstituted or substituted with one to five $R^1$ substituents;
each $R^1$ is independently selected from the group consisting of:
halogen,
cyano,
hydroxy,
$C_{1-6}$ alkyl, optionally substituted with one to five fluorines, and
$C_{1-6}$ alkoxy, optionally substituted with one to five fluorines;
$R^2$ is selected from the group consisting of
$C_{1-10}$ alkyl, wherein alkyl is optionally substituted with one to five substituents independently selected from fluorine and hydroxyl; and $(CH_2)_m$—$C_{3-6}$ cycloalkyl, wherein cycloalkyl is optionally substituted with one to three substituents independently selected from halogen, hydroxy, cyano, nitro, $CO_2H$, $C_{1-6}$ alkyloxycarbonyl, $C_{1-6}$ alkyl, and $C_{1-6}$ alkoxy, wherein alkyl and alkoxy are optionally substituted with one to five fluorines,
X and Y are each independently selected from the group consisting of $(CH_2)_n$, $(CH_2)_m$—O—$(CH_2)_m$, $(CH_2)_m$—S—$(CH_2)_m$, $(CH_2)_m$—$(CHF)_n$—$(CH_2)_m$ and $(CH_2)_m$—$(CF_2)_n$—$(CH_2)_m$, provided that when Y is $CH_2$, and X is selected from the group consisting of $(CH_2)_3$, $OCH_2$, and $OCH_2CH_2$, W is not phenyl;
n is selected from the group consisting of 1, 2 and 3; and
m is selected from the group consisting of 0, 1, 2, and 3.

With regard to the compounds described herein W is selected from the group consisting of phenyl, napthyl, heteroaryl and non-aromatic heterocyclyl. In certain embodiments of the compounds described herein, W is phenyl. In other embodiments, W is napthyl. In still other embodiments, W is a heteroaryl. Suitable heteroaryls include, but are not limited to, 2-thienyl, 3-thienyl, 2-furanyl, 3-furanyl, benzothiophenyl and pyridyl. In yet other embodiments, W is a non-aromatic heterocyclic. Suitable non-aromatic heterocyclyls include but are not limited to, tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, pyrrolidinone, oxazolidin-2-one, imidazolidine-2-one and pyridone.

Additionally, when W is phenyl, napthyl, heteroaryl and non-aromatic heterocyclyl, the phenyl, napthyl, pyridyl, quinolyl, heteroaryl and non-aromatic heterocyclyl are unsubstituted or substituted with one to five $R^1$ substituents. In certain embodiments, the phenyl, napthyl, and non-aromatic heterocyclyl are unsubstituted. In other embodiments, the phenyl, napthyl, heteroaryl and non-aromatic heterocyclyl are substituted with one to five $R^1$ substituents.

$R^1$ is independently selected from the group consisting of halogen, cyano, hydroxy, $C_{1-6}$ alkyl, optionally substituted with one to five fluorines, and $C_{1-6}$ alkoxy, optionally substituted with one to five fluorines. In certain embodiments, $R^1$ is halogen. Suitable halogens include, but are not limited to, fluorine, chlorine and bromine. In other embodiments, $R^1$ is cyano. In still other embodiments, $R^1$ is hydroxyl. In yet other embodiments, $R^1$ is $C_{1-6}$ alkyl. Suitable alkyls include, but are not limited to, methyl, ethyl and propyl. Alkyls can be optionally substituted with one to five fluorines. Suitable substituted alkyls include but are not limited to, trifluoromethyl. In other embodiments, $R^1$ is $C_{1-6}$ alkoxy. Suitable alkoxys include, but are not limited to, methoxy, ethoxy and propoxy. Alkoxys can be optionally substituted with one to five fluorines. Suitable substituted alkoxys include but are not limited to, trifluoromethoxy.

In certain embodiments, described herein, W is optionally substituted with one to three substituents independently selected from the group consisting of fluorine, chlorine, bromine, methyl, trifluoromethyl, and trifluoromethoxy. In one embodiment W is 2,5-difluorophenyl or 2,4,5-trifluorophenyl.

With regard to the compounds described herein, X and Y are each independently selected from the group consisting of $(CH_2)_n$, $(CH_2)_m$—O—$(CH_2)_m$, $(CH_2)_m$—S—$(CH_2)_m$, $(CH_2)_m$—$(CHF)_n$—$(CH_2)_m$ and $(CH_2)_m$—$(CF_2)_n$—$(CH_2)_m$. In some embodiments, X is selected from the group consisting of $(CH_2)_n$, $(CH_2)_m$—O—$(CH_2)_m$, $(CH_2)_m$—S—$(CH_2)_m$, $(CH_2)_m$—$(CHF)_n$—$(CH_2)_m$ and $(CH_2)_m$—$(CF_2)_n$—$(CH_2)_m$.

In certain embodiments, X is $(CH_2)_n$. In other embodiments, X is $(CH_2)_m$—O—$(CH_2)_m$. In still other embodiments, X is $(CH_2)_m$—(CHF)$_n$—$(CH_2)_m$. In yet other embodiments, X is $(CH_2)_m$—$(CF_2)_n$—$(CH_2)_m$. In other embodiments, X is $(CH_2)_m$—S—$(CH_2)_m$.

In some embodiments, Y is selected from the group consisting of $(CH_2)_n$, $(CH_2)_m$—O—$(CH_2)_m$, $(CH_2)_m$—S—$(CH_2)_m$, $(CH_2)_m$—(CHF)$_n$—$(CH_2)_m$ and $(CH_2)_m$—$(CF_2)_n$—$(CH_2)_m$. In certain embodiments, Y is $(CH_2)_n$. In other embodiments, Y is $(CH_2)_m$—O—$(CH_2)_m$. In still other embodiments, Y is $(CH_2)_m$—(CHF)$_n$—$(CH_2)_m$. In yet other embodiments, Y is $(CH_2)_m$—$(CF_2)_n$—$(CH_2)_m$. In other embodiments, Y is $(CH_2)_m$—S—$(CH_2)_m$.

With respect to the compounds described herein, n is selected from the group consisting of 1, 2 and 3 and m is selected from the group consisting of 0, 1, 2, and 3. In certain embodiments, n is 1. In other embodiments, n is 2. In still other embodiments, n is 3. In certain embodiments, m is 0. In other embodiments, m is 1. In still other embodiments, m is 2. In yet other embodiments, m is 3.

In certain embodiments of the compounds described herein, when Y is $CH_2$, and X is $(CH_2)_3$, W is not phenyl. In other embodiments, when Y is $CH_2$, and X is $OCH_2$, W is not phenyl. In still other embodiments, when Y is $CH_2$, and X is $OCH_2CH_2$, W is not phenyl. In yet other embodiments, when Y is $CH_2$, and X is $CH_2CH_2$, W is not phenyl. In certain embodiments, when Y is $CH_2$, and X is selected from the group consisting of $(CH_2)_3$, $OCH_2$, and $OCH_2CH_2$, W is not phenyl.

In certain embodiments of the compounds described herein, Y is —$CH_2$—. In other embodiments, Y is —$CH_2CH_2$—. In still other embodiments, Y is —$OCH_2$—. In still other embodiments, Y is —$CH_2O$—. In yet other embodiments, Y is —$OCH_2CH_2$—. In yet other embodiments, Y is —$CH_2OCH_2$—. In yet other embodiments, Y is —$CH_2CH_2O$—. In certain embodiments, Y is —$CF_2$—. In certain embodiments, Y is —CFH—. In other embodiments, Y is —$CF_2CH_2$—. In other embodiments, Y is —$CH_2CF_2$—. In other embodiments, Y is —CFHCH$_2$—. In other embodiments, Y is —$CH_2$CFH—. In other embodiments, Y is —(CFH)$_2$—. In still other embodiments, Y is —$SCH_2$—. In still other embodiments, Y is —$CH_2S$—. In still other embodiments, Y is —$SCH_2CH_2$—.

In certain embodiments of the compounds described herein, X is —$CH_2$—. In other embodiments, X is —$CH_2CH_2$—. In still other embodiments, X is —$OCH_2$—. In still other embodiments, X is —$SCH_2$—. In still other embodiments, X is —$CH_2O$—. In still other embodiments, X is —$CH_2S$—. In yet other embodiments, X is —$OCH_2CH_2$—. In yet other embodiments, X is —$CH_2OCH_2$—. In yet other embodiments, X is —$CH_2CH_2O$—. In certain embodiments, X is —$CF_2$—. In certain embodiments, X is —CFH—. In other embodiments, X is —$CF_2CH_2$—. In other embodiments, X is —$CH_2CF_2$—. In other embodiments, X is —CFHCH$_2$—. In other embodiments, X is —$CH_2$CFH—. In other embodiments, X is —(CFH)$_2$—. In still other embodiments, Y is —$SCH_2CH_2$—.

With regard to the compounds described herein, $R^2$ is selected from the group consisting of $C_{1-10}$ alkyl, wherein alkyl is optionally substituted with one to five substituents independently selected from fluorine and hydroxyl; and $(CH_2)_n$—$C_{3-6}$ cycloalkyl, wherein cycloalkyl is optionally substituted with one to three substituents independently selected from halogen, hydroxy, cyano, nitro, $CO_2H$, $C_{1-6}$ alkyloxycarbonyl, $C_{1-6}$ alkyl, and $C_{1-6}$ alkoxy, wherein alkyl and alkoxy are optionally substituted with one to five fluorines.

In certain embodiments, $R^2$ is $C_{1-10}$ alkyl. Suitable alkyls include, but are not limited to, methyl, ethyl, propyl, isopropyl, butyl, sec- and tert-butyl, pentyl, hexyl, heptyl, octyl and nonyl. Such alkyls can be unsubstituted. Alternatively, such alkyls can be substituted with one to five substituents independently selected from fluorine and hydroxyl. In certain embodiments, the alkyl is substituted with one hydroxyl. In other embodiments, the alkyl can be substituted with 1-3 flourines.

In certain embodiments, $R^2$ is $(CH_2)_m$—$C_{3-6}$ cycloalkyl, wherein cycloalkyl is optionally substituted with one to three substituents independently selected from halogen, hydroxy, cyano, nitro, $CO_2H$, $C_{1-6}$ alkyloxycarbonyl, $C_{1-6}$ alkyl, and $C_{1-6}$ alkoxy, wherein alkyl and alkoxy are optionally substituted with one to five fluorines. In certain embodiments, $R^2$ is $(CH_2)_n$—$C_{3-6}$ cycloalkyl, wherein in m is described above. Suitable cycloalkyls include, but are not limited to, cyclopropyl, cyclobutyl, cyclopentyl, cyclohexyl, cycloheptyl and cyclooctyl. Such cycloalkyls can be unsubstituted. Alternatively, such cycloalkyls can be substituted with one to three substituents independently selected from halogen, hydroxy, cyano, nitro, $CO_2H$, $C_{1-6}$ alkyloxycarbonyl, $C_{1-6}$ alkyl, and $C_{1-6}$ alkoxy, wherein alkyl and alkoxy are optionally substituted with one to five fluorines. In certain embodiments, the cycloalkyl is substituted with one to three halogens. Suitable halogens include, but are not limited to, fluorine, chlorine and bromine. In other embodiments, the cycloalkyl is substituted with hydroxyl. In still other embodiments, the cycloalkyl is substituted with cyano. In yet another embodiment, the cycloalkyl is substituted with nitro. In certain embodiments, the cycloalkyl is substituted with $CO_2H$.

In other embodiments, the cycloalkyl is substituted with $C_{1-6}$ alkyloxycarbonyl. Suitable alkyloxycarbonyls include, but are not limited to, methyloxycarbonyl (MeOCO—), ethyloxycarbonyl, or butyloxycarbonyl. In still other embodiments, the cycloalkyls are substituted with $C_{1-6}$ alkyl. Suitable alkyls include, but are not limited to, methyl, ethyl and propyl. Such alkyls can be optionally substituted with one to five fluorines. Suitable substituted alkyls include but are not limited to, trifluoromethyl. In yet other embodiments, the cycloalkyls are substituted with $C_{1-6}$ alkoxy. Suitable alkoxys include, but are not limited to, methoxy, ethoxy and propoxy. Alkoxys can be optionally substituted with one to five fluorines. Suitable substituted alkoxys include but are not limited to, trifluoromethoxy.

In certain embodiments, $R^2$ is selected from the group consisting of —$C_{1-6}$ alkyl, and —$C_{3-6}$ cycloalkyl. In other embodiments, $R^2$ is $C_{1-6}$ alkyl or —$C_{3-6}$ cycloalkyl, wherein alkyl and cycloalkyl are optionally substituted with one to five fluorines In certain embodiment of the compounds described herein, the compounds have structural Formula Ia or Ib having the indicated stereochemical configuration at the two stereogenic carbon atoms marked with an *:

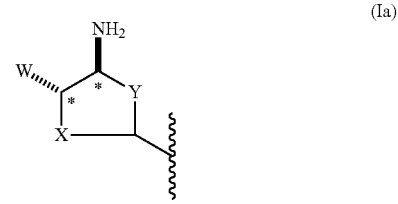

(Ia)

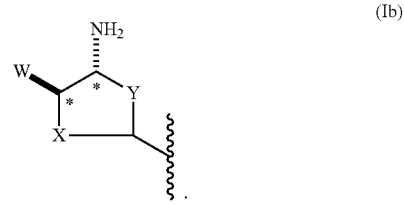

(Ib)

In certain embodiments, the compounds have structural Formula Ia having the indicated absolute stereochemical configuration at the two stereogenic carbon atoms marked with an *:

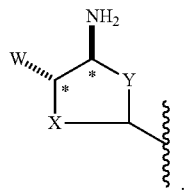

(Ia)

In certain embodiments, the compounds have structural Formula Ia having the indicated absolute stereochemical configuration at the two stereogenic carbon atoms marked with an *:

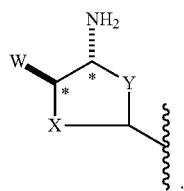

(Ib)

In other embodiments, the compounds described herein have structural formulae Ic or Id having the indicated stereochemical configuration at the three stereogenic carbon atoms marked with an *:

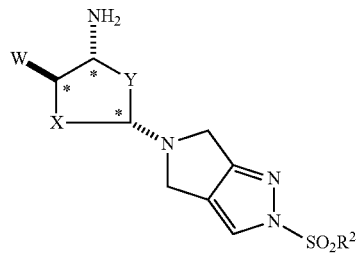

(Ic)

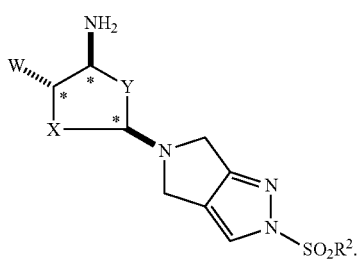

(Id)

In certain embodiments the compounds described herein structural Formula Ic having the indicated absolute stereochemical configuration at the three stereogenic carbon atoms marked with an *:

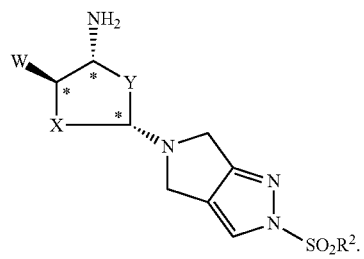

(Ic)

In certain embodiments the compounds described herein structural Formula Id having the indicated absolute stereochemical configuration at the three stereogenic carbon atoms marked with an *:

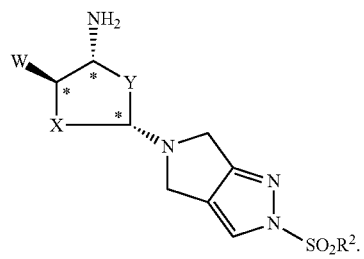

(Id)

Nonlimiting examples of compounds of the present invention that are useful as dipeptidyl peptidase-IV inhibitors are as follows:

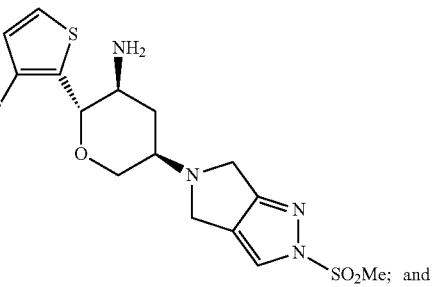

and

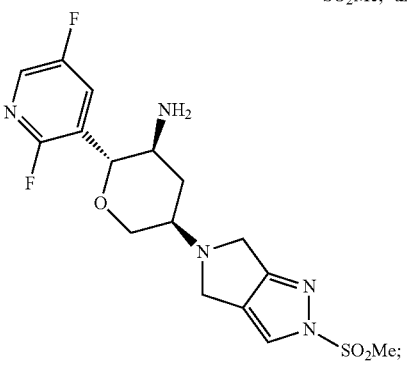

and pharmaceutically acceptable salts thereof.

As used herein the following definitions are applicable.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Where the specified number of carbon atoms permits, e.g., from $C_{3-10}$, the term alkyl also includes cycloalkyl groups, and combinations of linear or branched alkyl chains combined with cycloalkyl structures. When no number of carbon atoms is specified, $C_{1-6}$ is intended.

"Cycloalkyl" is a subset of alkyl and means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

The term "alkoxy" refers to straight or branched chain alkoxides of the number of carbon atoms specified (e.g., $C_{1-10}$ alkoxy), or any number within this range [i.e., methoxy (MeO—), ethoxy, isopropoxy, etc].

The term "alkylsulfonyl" refers to straight or branched chain alkylsulfones of the number of carbon atoms specified (e.g., $C_{1-6}$ alkylsulfonyl), or any number within this range [i.e., methylsulfonyl ($MeSO_2$—), ethylsulfonyl, isopropylsulfonyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

The term "heterocyclyl" refers to saturated or unsaturated non-aromatic rings or ring systems containing at least one heteroatom selected from O, S and N, further including the oxidized forms of sulfur, namely SO and $SO_2$. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, pyrrolidinone, oxazolidin-2-one, imidazolidine-2-one, pyridone, and the like.

"Heteroaryl" means an aromatic or partially aromatic heterocycle that contains at least one ring heteroatom selected from O, S and N. Heteroaryls also include heteroaryls fused to other kinds of rings, such as aryls, cycloalkyls and heterocycles that are not aromatic. Examples of heteroaryl groups include pyrrolyl, isoxazolyl, isothiazolyl, pyrazolyl, pyridinyl, 2-oxo-(1H)-pyridinyl (2-hydroxy-pyridinyl), oxazolyl, 1,2,4-oxadiazolyl, 1,3,4-oxadiazolyl, thiadiazolyl, thiazolyl, imidazolyl, triazolyl, tetrazolyl, furyl, triazinyl, thienyl, pyrimidinyl, pyrazinyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, imidazo[1,2-a]pyridinyl, [1,2,4-triazolo][4,3-a]pyridinyl, pyrazolo[1,5-a]pyridinyl, [1,2,4-triazolo][1,5-c]pyridinyl, 2-oxo-1,3-benzoxazolyl, 4-oxo-3H-quinazolinyl, 3-oxo-[1,2,4]-triazolo[4,3-a]-2H-pyridinyl, 5-oxo-[1,2,4]-4H-oxadiazolyl, 2-oxo-[1,3,4]-3H-oxadiazolyl, 2-oxo-1,3-dihydro-2H-imidazolyl, 3-oxo-2,4-dihydro-3H-1,2,4-triazolyl, and the like. For heterocyclyl and heteroaryl groups, rings and ring systems containing from 3-15 atoms are included, forming 1-3 rings.

"Halogen" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

The compounds of the present invention contain one or more asymmetric centers and can thus occur as racemates, racemic mixtures, single enantiomers, diastereomeric mixtures, and individual diastereomers. In particular the compounds of the present invention have an asymmetric center at the stereogenic carbon atoms marked with an * in formulae Ia, Ib, Ic and Id. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

Formula I shows the structure of the class of compounds without preferred stereochemistry. Formulae Ia and Ib show the preferred stereochemistry at the stereogenic carbon atoms to which are attached the $NH_2$ and W groups on the ring. Formulae Ic and Id show the preferred stereochemistry at the stereogenic carbon atoms to which are attached the $NH_2$, W, and dihydropyrrolopyrazole on the ring.

The independent syntheses of these diastereomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Solvates, and in particular, the hydrates of the compounds of structural formula I are included in the present invention as well.

Exemplifying the invention is the use of the compounds disclosed in the Examples and herein.

The subject compounds are useful in a method of inhibiting the dipeptidyl peptidase-IV enzyme in a patient such as a mammal in need of such inhibition comprising the administration of an effective amount of the compound. The present invention is directed to the use of the compounds disclosed herein as inhibitors of dipeptidyl peptidase-IV enzyme activity.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The present invention is further directed to a method for the manufacture of a medicament for inhibiting dipeptidyl peptidase-IV enzyme activity in humans and animals comprising combining a compound of the present invention with a pharmaceutically acceptable carrier or diluent. More particularly, the present invention is directed to the use of a compound of structural formula I in the manufacture of a medicament for use in treating a condition selected from the group consisting of hyperglycemia, Type 2 diabetes, obesity, and a lipid disorder in a mammal, wherein the lipid disorder is selected from the group consisting of dyslipidemia, hyperlipidemia, hypertriglyceridemia, hypercholesterolemia, low HDL, and high LDL.

The subject treated in the present methods is generally a mammal, preferably a human being, male or female, in whom inhibition of dipeptidyl peptidase-IV enzyme activity is desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibitors of dipeptidyl peptidase-IV enzyme activity may be demonstrated by methodology known in the art. Inhibition constants are determined as follows. A continuous fluorometric assay is employed with the substrate Gly-Pro-AMC, which is cleaved by DPP-4 to release the fluorescent AMC leaving group. The kinetic parameters that describe this reaction are as follows: $K_m=50$ µM; $k_{cat}=75\,s^{-1}$; $k_{cat}/K_m=1.5\times10^6\,M^{-1}\,s^{-1}$. A typical reaction contains approximately 50 pM enzyme, 50 µM Gly-Pro-AMC, and buffer (100 mM HEPES, pH 7.5, 0.1 mg/ml BSA) in a total reaction volume of 100 µL. Liberation of AMC is monitored continuously in a 96-well plate fluorometer using an excitation wavelength of 360 nm and an emission wavelength of 460 nm. Under these conditions, approximately 0.8 µM AMC is produced in 30 minutes at 25 degrees C. The enzyme used in these studies was soluble (transmembrane domain and cytoplasmic extension excluded) human protein produced in a baculovirus expression system (Bac-To-Bac, Gibco BRL). The kinetic constants for hydrolysis of Gly-Pro-AMC and GLP-1 were found to be in accord with literature values for the native enzyme. To measure the dissociation constants for compounds, solutions of inhibitor in DMSO were added to reactions containing enzyme and substrate (final DMSO concentration is 1%). All experiments were conducted at room temperature using the standard reaction conditions described above. To determine the dissociation constants ($K_i$), reaction rates were fit by non-linear regression to the Michaelis-Menton equation for competitive inhibition. The errors in reproducing the dissociation constants are typically less than two-fold.

The compounds of structural formula (I), particularly the compounds of Examples 1-2 shown below, had activity in inhibiting the dipeptidyl peptidase-IV enzyme in the aforementioned assays, generally with an $IC_{50}$ of less than about 1 µM, and more typically of less than 0.1 µM. Such results are indicative of the intrinsic activity of the compounds of the present invention for use as inhibitors the dipeptidyl peptidase-IV enzyme activity.

Dipeptidyl peptidase-IV enzyme (DPP-4) is a cell surface protein that has been implicated in a wide range of biological functions. It has a broad tissue distribution (intestine, kidney, liver, pancreas, placenta, thymus, spleen, epithelial cells, vascular endothelium, lymphoid and myeloid cells, serum), and distinct tissue and cell-type expression levels. DPP-4 is identical to the T cell activation marker CD26, and it can cleave a number of immunoregulatory, endocrine, and neurological peptides in vitro. This has suggested a potential role for this peptidase in a variety of disease processes in humans or other species.

Accordingly, the subject compounds are useful in a method for the prevention or treatment of the following diseases, disorders and conditions.

Type II Diabetes and Related Disorders: It is well established that the incretins GLP-1 and GIP are rapidly inactivated in vivo by DPP-4. Studies with DPP-4$^{(-/-)}$-deficient mice and preliminary clinical trials indicate that DPP-4 inhibition increases the steady state concentrations of GLP-1 and GIP, resulting in improved glucose tolerance. By analogy to GLP-1 and GIP, it is likely that other glucagon family peptides involved in glucose regulation are also inactivated by DPP-4 (eg. PACAP). Inactivation of these peptides by DPP-4 may also play a role in glucose homeostasis. The DPP-4 inhibitors of the present invention therefore have utility in the treatment of type II diabetes and in the treatment and prevention of the numerous conditions that often accompany Type II diabetes, including Syndrome X (also known as Metabolic Syndrome), reactive hypoglycemia, and diabetic dyslipidemia. Obesity, discussed below, is another condition that is often found with Type II diabetes that may respond to treatment with the compounds of this invention.

The following diseases, disorders and conditions are related to Type 2 diabetes, and therefore may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component. In Syndrome X, also known as Metabolic Syndrome, obesity is thought to promote insulin resistance, diabetes, dyslipidemia, hypertension, and increased cardiovascular risk. Therefore, DPP-4 inhibitors may also be useful to treat hypertension associated with this condition.

Obesity: DPP-4 inhibitors may be useful for the treatment of obesity. This is based on the observed inhibitory effects on food intake and gastric emptying of GLP-1 and GLP-2. Exogenous administration of GLP-1 in humans significantly decreases food intake and slows gastric emptying (*Am. J. Physiol.*, 277: R910-R916 (1999)). ICV administration of GLP-1 in rats and mice also has profound effects on food intake (*Nature Medicine*, 2: 1254-1258 (1996)). This inhibition of feeding is not observed in GLP-1R$^{(-/-)}$ mice, indicating that these effects are mediated through brain GLP-1 receptors. By analogy to GLP-1, it is likely that GLP-2 is also regulated by DPP-4. ICV administration of GLP-2 also inhibits food intake, analogous to the effects observed with GLP-1 (*Nature Medicine*, 6: 802-807 (2000)). In addition, studies with DPP-4 deficient mice suggest that these animals are resistant to diet-induced obesity and associated pathology (e.g. hyperinsulinonemia).

Cardiovascular Disease: GLP-1 has been shown to be beneficial when administered to patients following acute myocardial infarction, leading to improved left ventricular function and reduced mortality after primary angioplasty (Circulation, 109: 962-965 (2004)). GLP-1 administration is also useful for the treatment of left ventricular systolic dysfunction in dogs with dilated cardiomyopathy and ischemic induced left ventricular dysfunction, and thus may prove useful for the treatment of patients with heart failure (US2004/0097411). DPP-4 inhibitors are expected to show similar effects through their ability to stabilize endogenous GLP-1.

Growth Hormone Deficiency: DPP-4 inhibition may be useful for the treatment of growth hormone deficiency, based on the hypothesis that growth-hormone releasing factor (GRF), a peptide that stimulates release of growth hormone from the anterior pituitary, is cleaved by the DPP-4 enzyme in vivo (WO 00/56297). The following data provide evidence that GRF is an endogenous substrate: (1) GRF is efficiently cleaved in vitro to generate the inactive product GRF[3-44]

(BBA 1122: 147-153 (1992)); (2) GRF is rapidly degraded in plasma to GRF[3-44]; this is prevented by the DPP-4 inhibitor diprotin A; and (3) GRF[3-44] is found in the plasma of a human GRF transgenic pig (*J. Clin. Invest.*, 83: 1533-1540 (1989)). Thus DPP-4 inhibitors may be useful for the same spectrum of indications which have been considered for growth hormone secretagogues.

Intestinal Injury: The potential for using DPP-4 inhibitors for the treatment of intestinal injury is suggested by the results of studies indicating that glucagon-like peptide-2 (GLP-2), a likely endogenous substrate for DPP-4, may exhibit trophic effects on the intestinal epithelium (*Regulatory Peptides*, 90: 27-32 (2000)). Administration of GLP-2 results in increased small bowel mass in rodents and attenuates intestinal injury in rodent models of colitis and enteritis.

Immunosuppression: DPP-4 inhibition may be useful for modulation of the immune response, based upon studies implicating the DPP-4 enzyme in T cell activation and in chemokine processing, and efficacy of DPP-4 inhibitors in in vivo models of disease. DPP-4 has been shown to be identical to CD26, a cell surface marker for activated immune cells. The expression of CD26 is regulated by the differentiation and activation status of immune cells. It is generally accepted that CD26 functions as a co-stimulatory molecule in in vitro models of T cell activation. A number of chemokines contain proline in the penultimate position, presumably to protect them from degradation by non-specific aminopeptidases. Many of these have been shown to be processed in vitro by DPP-4. In several cases (RANTES, LD78-beta, MDC, eotaxin, SDF-1alpha), cleavage results in an altered activity in chemotaxis and signaling assays. Receptor selectivity also appears to be modified in some cases (RANTES). Multiple N-terminally truncated forms of a number of chemokines have been identified in in vitro cell culture systems, including the predicted products of DPP-4 hydrolysis.

DPP-4 inhibitors have been shown to be efficacious immunosuppressants in animal models of transplantation and arthritis. Prodipine (Pro-Pro-diphenyl-phosphonate), an irreversible inhibitor of DPP-4, was shown to double cardiac allograft survival in rats from day 7 to day 14 (*Transplantation*, 63: 1495-1500 (1997)). DPP-4 inhibitors have been tested in collagen and alkyldiamine-induced arthritis in rats and showed a statistically significant attenuation of hind paw swelling in this model [*Int. J. Immunopharmacology*, 19:15-24 (1997) and *Immunopharmacology*, 40: 21-26 (1998)]. DPP-4 is upregulated in a number of autoimmune diseases including rheumatoid arthritis, multiple sclerosis, Graves' disease, and Hashimoto's thyroiditis (*Immunology Today*, 20: 367-375 (1999)).

HIV Infection: DPP-4 inhibition may be useful for the treatment or prevention of HIV infection or AIDS because a number of chemokines which inhibit HIV cell entry are potential substrates for DPP-4 (*Immunology Today* 20: 367-375 (1999)). In the case of SDF-1alpha, cleavage decreases antiviral activity (*PNAS*, 95: 6331-6 (1998)). Thus, stabilization of SDF-1alpha through inhibition of DPP-4 would be expected to decrease HIV infectivity.

Hematopoiesis: DPP-4 inhibition may be useful for the treatment or prevention of hematopiesis because DPP-4 may be involved in hematopoiesis. A DPP-4 inhibitor, Val-Boro-Pro, stimulated hematopoiesis in a mouse model of cyclophosphamide-induced neutropenia (WO 99/56753).

Neuronal Disorders: DPP-4 inhibition may be useful for the treatment or prevention of various neuronal or psychiatric disorders because a number of peptides implicated in a variety of neuronal processes are cleaved in vitro by DPP-4. A DPP-4 inhibitor thus may have a therapeutic benefit in the treatment of neuronal disorders. Endomorphin-2, beta-casomorphin, and substance P have all been shown to be in vitro substrates for DPP-4. In all cases, in vitro cleavage is highly efficient, with $k_{cat}/K_m$ about $10^6$ $M^{-1}$ $s^{-1}$ or greater. In an electric shock jump test model of analgesia in rats, a DPP-4 inhibitor showed a significant effect that was independent of the presence of exogenous endomorphin-2 (*Brain Research*, 815: 278-286 (1999)). Neuroprotective and neuroregenerative effects of DPP-4 inhibitors were also evidenced by the inhibitors' ability to protect motor neurons from excitotoxic cell death, to protect striatal innervation of dopaminergic neurons when administered concurrently with MPTP, and to promote recovery of striatal innervation density when given in a therapeutic manner following MPTP treatment [see Yong-Q. Wu, et al., "Neuroprotective Effects of Inhibitors of Dipeptidyl peptidase-IV In Vitro and In Vivo," *Int. Conf. On Dipeptidyl Aminopeptidases: Basic Science and Clinical Applications*, Sep. 26-29, 2002 (Berlin, Germany)].

Anxiety: Rats naturally deficient in DPP-4 have an anxiolytic phenotype (WO 02/34243; Karl et al., *Physiol. Behav.* 2003). DPP-4 deficient mice also have an anxiolytic phenotype using the porsolt and light/dark models. Thus DPP-4 inhibitors may prove useful for treating anxiety and related disorders.

Memory and Cognition: GLP-1 agonists are active in models of learning (passive avoidance, Morris water maze) and neuronal injury (kainate-induced neuronal apoptosis) as demonstrated by During et al. (*Nature Med.* 9: 1173-1179 (2003)). The results suggest a physiological role for GLP-1 in learning and neuroprotection. Stabilization of GLP-1 by DPP-4 inhibitors are expected to show similar effects Myocardial Infarction: GLP-1 has been shown to be beneficial when administered to patients following acute myocardial infarction (Circulation, 109: 962-965 (2004)). DPP-4 inhibitors are expected to show similar effects through their ability to stabilize endogenous GLP-1.

Tumor Invasion and Metastasis: DPP-4 inhibition may be useful for the treatment or prevention of tumor invasion and metastasis because an increase or decrease in expression of several ectopeptidases including DPP-4 has been observed during the transformation of normal cells to a malignant phenotype (*J. Exp. Med.*, 190: 301-305 (1999)). Up- or down-regulation of these proteins appears to be tissue and cell-type specific. For example, increased CD26/DPP-4 expression has been observed on T cell lymphoma, T cell acute lymphoblastic leukemia, cell-derived thyroid carcinomas, basal cell carcinomas, and breast carcinomas. Thus, DPP-4 inhibitors may have utility in the treatment of such carcinomas.

Benign Prostatic Hypertrophy: DPP-4 inhibition may be useful for the treatment of benign prostatic hypertrophy because increased DPP-4 activity was noted in prostate tissue from patients with BPH (*Eur. J. Clin. Chem. Clin. Biochem.*, 30: 333-338 (1992)).

Sperm Motility/Male Contraception: DPP-4 inhibition may be useful for the altering sperm motility and for male contraception because in seminal fluid, prostatosomes, prostate derived organelles important for sperm motility, possess very high levels of DPP-4 activity (*Eur. J. Clin. Chem. Clin. Biochem.*, 30: 333-338 (1992)).

Gingivitis: DPP-4 inhibition may be useful for the treatment of gingivitis because DPP-4 activity was found in gingival crevicular fluid and in some studies correlated with periodontal disease severity (*Arch. Oral Biol.*, 37: 167-173 (1992)).

Osteoporosis: DPP-4 inhibition may be useful for the treatment or prevention of osteoporosis because GIP receptors are present in osteoblasts.

Stem Cell Transplantation: Inhibition of DPP-4 on donor stem cells has been shown to lead to an enhancement of their bone marrow homing efficiency and engraftment, and an increase in survival in mice (Christopherson, et al., *Science*, 305:1000-1003 (2004)). Thus DPP-4 inhibitors may be useful in bone marrow transplantation.

The compounds of the present invention have utility in treating or preventing one or more of the following conditions or diseases: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), (25) Type 2 diabetes, (26) growth hormone deficiency, (27) neutropenia, (28) neuronal disorders, (29) tumor metastasis, (30) benign prostatic hypertrophy, (32) gingivitis, (33) hypertension, (34) osteoporosis, (35) anxiety, (36) memory deficit, (37) cognition deficit, (38) stroke, (39) Alzheimer's disease, and other conditions that may be treated or prevented by inhibition of DPP-4.

The compounds of the present invention are further useful in methods for the prevention or treatment of the aforementioned diseases, disorders and conditions in combination with other therapeutic agents.

The compounds of the present invention may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefore, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered separately or in the same pharmaceutical composition in combination with a compound of the formulas described herein include, but are not limited to:

(1) other dipeptidyl peptidase-IV (DPP-4) inhibitors (e.g., sitagliptin, alogliptin, linagliptin, vildagliptin);

(2) insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ □dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SP-PARγM's), (e.g., such as those disclosed in WO 02/060388, WO 02/08188, WO 2004/019869, WO 2004/020409, WO 2004/020408, and WO 2004/066963); and (4) PPARγ □partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814);

(3) insulin or insulin analogs (e.g., insulin detemir, insulin glulisine, insulin degludec, insulin glargine, insulin lispro and inhalable formulations of each);

(4) leptin and leptin derivatives and agonists;

(5) amylin and amylin analogs (e.g., pramlintide);

(6) sulfonylurea and non-sulfonylurea insulin secretagogues (e.g., tolbutamide, glyburide, glipizide, glimepiride, mitiglinide, meglitinides, nateglinide and repaglinide);

(7) α-glucosidase inhibitors (e.g., acarbose, voglibose and miglitol);

(8) glucagon receptor antagonists (e.g., such as those disclosed in WO 98/04528, WO 99/01423, WO 00/39088, and WO 00/69810);

(9) incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof);

(10) LDL cholesterol lowering agents such as (i) HMG-CoA reductase inhibitors (e.g., simvastatin, lovastatin, pravastatin, crivastatin, fluvastatin, atorvastatin, pitavastatin and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA:cholesterol acyltransferase inhibitors, (e.g., avasimibe);

(11) HDL-raising drugs, (e.g., niacin and nicotinic acid receptor agonists, and extended-release versions thereof; MK-524A, which is a combination of niacin extended-release and the DP-1 antagonist MK-524);

(12) antiobesity compounds;

(13) agents intended for use in inflammatory conditions, such as aspirin, non-steroidal anti-inflammatory drugs or NSAIDs, glucocorticoids, and selective cyclooxygenase-2 or COX-2 inhibitors;

(14) antihypertensive agents, such as ACE inhibitors (e.g., lisinopril, enalapril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers, and calcium channel blockers;

(15) glucokinase activators (GKAs) (e.g., AZD6370);

(16) inhibitors of 11β-hydroxysteroid dehydrogenase type 1, (e.g., such as those disclosed in U.S. Pat. No. 6,730,690, and LY-2523199);

(17) CETP inhibitors (e.g., anacetrapib, and torcetrapib);

(18) inhibitors of fructose 1,6-bisphosphatase, (e.g., such as those disclosed in U.S. Pat. Nos. 6,054,587; 6,110,903; 6,284,748; 6,399,782; and 6,489,476);

(19) inhibitors of acetyl CoA carboxylase-1 or 2 (ACC1 or ACC2);

(20) AMP-activated Protein Kinase (AMPK) activators;

(21) other agonists of the G-protein-coupled receptors: (i) GPR-109, (ii) GPR-119 (e.g., MBX2982 and PSN821), and (iii) GPR-40 (e.g., TAK875, 5-[4-[[(1R)-4-[6-(3-hydroxy-3-methylbutoxy)-2-methylpyridine-3-yl]-2,3-dihydro-1H-indene-1-yl]oxy]phenyl]isothiazole-3-ol 1-oxide, 5-(4-((3-(2,6-dimethyl-4-(3-(methylsulfonyl)propoxy)phenyl)phenyl)methoxy)phenyl) iso, 5-(4-((3-(2-methyl-6-(3-hydroxypropoxy)pyridine-3-yl)-2-methylphenyl)methoxy)phenyl)isothiazole-3-ol 1-oxide, and 5-[4-[[3-[4-(3-aminopropoxy)-2,6-dimethylphenyl]phenyl]methoxy]phenyl]isothiazole-3-ol 1-oxide);

(22) SSTR3 antagonists (e.g., such as those disclosed in WO 2009/001836);

(23) neuromedin U receptor agonists (e.g., such as those disclosed in WO 2009/042053, including, but not limited to, neuromedin S (NMS));

(24) SCD inhibitors;

(25) GPR-105 antagonists (e.g., such as those disclosed in WO 2009/000087);

(26) SGLT inhibitors (e.g., ASP1941, SGLT-3, empagliflozin, dapagliflozin, canagliflozin, BI-10773, PF-04971729, remogliflozin, TS-071, tofogliflozin, ipragliflozin, and LX-4211);

(27) inhibitors of acyl coenzyme A:diacylglycerol acyltransferase 1 and 2 (DGAT-1 and DGAT-2);

(28) inhibitors of fatty acid synthase;

(29) inhibitors of acyl coenzyme A:monoacylglycerol acyltransferase 1 and 2 (MGAT-1 and MGAT-2);

(30) agonists of the TGR5 receptor (also known as GPBAR1, BG37, GPCR19, GPR131, and M-BAR);

(31) ileal bile acid transporter inhibitors;

(32) PACAP, PACAP mimetics, and PACAP receptor 3 agonists;

(33) PPAR agonists;

(34) protein tyrosine phosphatase-1B (PTP-1B) inhibitors;

(35) IL-1b antibodies, (e.g., XOMA052 and canakinumab); and

(36) bromocriptine mesylate and rapid-release formulations thereof.

Of particular interest are metformin hydrochloride, pioglitazone, rosiglitazone, simvastatin, atorvastatin, or a sulfonylurea.

Other dipeptidyl peptidase-IV (DPP-4) inhibitors that can be used in combination with compounds of the formulas described herein include, but are not limited to:

(2R,3S,5R)-5-(1-methyl-4,6-dihydropyrrolo[3,4-c]pyrazol-5(1H)-yl)-2-(2,4,5-trifluorophenyl)tetrahydro-2H-pyran-3-amine;

(2R,3S,5R)-5-(1-methyl-4,6-dihydropyrrolo[3,4-c]pyrazol-5(1H)-yl)-2-(2,4,5-trifluorophenyl)tetrahydro-2H-pyran-3-amine;

(2R,3S,5R)-2-(2,5-difluorophenyl)tetrahydro)-5-(4,6-dihydropyrrolo[3,4-c]pyrazol-5(1H)-yl) tetrahydro-2H-pyran-3-amine;

(3R)-4-[(3R)-3-amino-4-(2,4,5-trifluorophenyl)butanoyl]-hexahydro-3-methyl-2H-1,4-diazepin-2-one;

4-[(3R)-3-amino-4-(2,5-difluorophenyl)butanoyl] hexahydro-1-methyl-2H-1,4-diazepin-2-one hydrochloride; and (3R)-4-[(3R)-3-amino-4-(2,4,5-trifluorophenyl)butanoyl]-hexahydro-3-(2,2,2-trifluoroethyl)-2H-1,4-diazepin-2-one; and pharmaceutically acceptable salts thereof.

Antiobesity compounds that can be combined with compounds of Formula I include topiramate; zonisamide; naltrexone; phentermine; bupropion; the combination of bupropion and naltrexone; the combination of bupropion and zonisamide; the combination of topiramate and phentermine; fenfluramine; dexfenfluramine; sibutramine; lipase inhibitors, such as orlistat and cetilistat; melanocortin receptor agonists, in particular, melanocortin-4 receptor agonists; CCK-1 agonists; melanin-concentrating hormone (MCH) receptor antagonists; neuropeptide $Y_1$ or $Y_5$ antagonists (such as MK-0557); CB1 receptor inverse agonists and antagonists (such as rimonabant and taranabant); $\beta_3$ adrenergic receptor agonists; ghrelin antagonists; bombesin receptor agonists (such as bombesin receptor subtype-3 agonists); and 5-hydroxytryptamine-2c (5-HT2c) agonists, such as lorcaserin. For a review of anti-obesity compounds that can be combined with compounds of the present invention, see S. Chaki et al., "Recent advances in feeding suppressing agents: potential therapeutic strategy for the treatment of obesity," *Expert Opin. Ther. Patents*, 11: 1677-1692 (2001); D. Spanswick and K. Lee, "Emerging antiobesity drugs," *Expert Opin. Emerging Drugs*, 8: 217-237 (2003); J. A. Fernandez-Lopez, et al., "Pharmacological Approaches for the Treatment of Obesity," *Drugs*, 62: 915-944 (2002); and K. M. Gadde, et al., "Combination pharmacological therapies for obesity," *Exp. Opin. Pharmacother.*, 10: 921-925 (2009).

Glucagon receptor antagonists that can be used in combination with the compounds of Formula I include, but are not limited to:

N-[4-((1S)-1-{3-(3,5-dichlorophenyl)-5-[6-(trifluoromethoxy)-2-naphthyl]-1H-pyrazol-1-yl}ethyl)benzoyl]-β-alanine;

N-[4-((1R)-1-{3-(3,5-dichlorophenyl)-5-[6-(trifluoromethoxy)-2-naphthyl]-1H-pyrazol-1-yl}ethyl)benzoyl]-β-alanine;

N-(4-{1-[3-(2,5-dichlorophenyl)-5-(6-methoxy-2-naphthyl)-1H-pyrazol-1-yl]ethyl}benzoyl)-β-alanine;

N-(4-{(1S)-1-[3-(3,5-dichlorophenyl)-5-(6-methoxy-2-naphthyl)-1H-pyrazol-1-yl]ethyl}benzoyl)-β-alanine;

N-(4-{(1S)-1-[(R)-(4-chlorophenyl)(7-fluoro-5-methyl-1H-indol-3-yl)methyl]butyl}benzoyl)-β-alanine; and N-(4-{(1S)-1-[(4-chlorophenyl)(6-chloro-8-methylquinolin-4-yl)methyl]butyl}benzoyl)-β-alanine; and pharmaceutically acceptable salts thereof.

Inhibitors of stearoyl-coenzyme A delta-9 desaturase (SCD) that can be used in combination with the compounds of Formula I include, but are not limited to:

[5-(5-{4-[2-(trifluoromethyl)phenoxy]piperidin-1-yl}-1,3,4-thiadiazol-2-yl)-2H-tetrazol-2-yl]acetic acid;

(2'-{4-[2-(trifluoromethyl)phenoxy]piperidin-1-yl}-2,5'-bi-1,3-thiazol-4-yl)acetic acid;

(5-{3-[4-(2-bromo-5-fluorophenoxy)piperidin-1-yl]isoxazol-5-yl}-2H-tetrazol-2-yl)acetic acid;

(3-{3-[4-(2-bromo-5-fluorophenoxy)piperidin-1-yl]-1,2,4-oxadiazol-5-yl}-1H-pyrrol-1-yl)acetic acid;

(5-{5-[4-(2-bromo-5-fluorophenoxy)piperidin-1-yl] pyrazin-2-yl}-2H-tetrazol-2-yl)acetic acid; and (5-{2-[4-(5-bromo-2-chlorophenoxy)piperidin-1-yl]pyrimidin-5-yl}-2H-tetrazol-2-yl)acetic acid;

and pharmaceutically acceptable salts thereof.

Glucokinase activators that can be used in combination with the compounds of Formula I, but are not limited to:

3-(6-ethanesulfonylpyridin-3-yloxy)-5-(2-hydroxy-1-methyl-ethoxy)-N-(1-methyl-1H-pyrazol-3-yl)benzamide;

5-(2-hydroxy-1-methyl-ethoxy)-3-(6-methanesulfonylpyridin-3-yloxy)-N-(1-methyl-1H-pyrazol-3-yl)benzamide;

5-(1-hydroxymethyl-propoxy)-3-(6-methanesulfonylpyridin-3-yloxy)-N-(1-methyl-1H-pyrazol-3-yl)benzamide;

3-(6-methanesulfonylpyridin-3-yloxy)-5-(1-methoxymethyl-propoxy)-N-(1-methyl-1H-pyrazol-3-yl)benzamide;

5-isopropoxy-3-(6-methanesulfonylpyridin-3-yloxy)-N-(1-methyl-1H-pyrazol-3-yl)benzamide;

5-(2-fluoro-1-fluoromethyl-ethoxy)-3-(6-methanesulfonylpyridin-3-yloxy)-N-(1-methyl-1H-pyrazol-3-yl)benzamide;

3-({4-[2-(dimethylamino)ethoxy]phenyl}thio)-N-(3-methyl-1,2,4-thiadiazol-5-yl)-6-[(4-methyl-4H-1,2,4-triazol-3-yl)thio]pyridine-2-carboxamide;
3-({4-[(1-methylazetidin-3-yl)oxy]phenyl}thio)-N-(3-methyl-1,2,4-thiadiazol-5-yl)-6-[(4-methyl-4H-1,2,4-triazol-3-yl)thio]pyridine-2-carboxamide;
N-(3-methyl-1,2,4-thiadiazol-5-yl)-6-[(4-methyl-4H-1,2,4-triazol-3-yl)thio]-3-{[4-(2-pyrrolidin-1-ylethoxy)phenyl]thio}pyridine-2-carboxamide; and
3-[(4-{2-[(2R)-2-methylpyrrolidin-1-yl]ethoxy}phenyl)thio-N-(3-methyl-1,2,4-thiadiazol-5-yl)-6-[(4-methyl-4H-1,2,4-triazol-3-yl)thio]pyridine-2-carboxamide; and pharmaceutically acceptable salts thereof.

Agonists of the GPR-119 receptor that can be used in combination with the compounds of Formula I include, but are not limited to:
rac-cis 5-chloro-2-{4-[2-(2-{[5-(methylsulfonyl)pyridin-2-yl]oxy}ethyl)cyclopropyl]piperidin-1-yl}pyrimidine;
5-chloro-2-{4-[(1R,2S)-2-(2-{[5-(methylsulfonyl)pyridin-2-yl]oxy}ethyl)cyclopropyl]piperidin-1-yl}pyrimidine;
rac cis-5-chloro-2-[4-(2-{2-[4-(methylsulfonyl)phenoxy]ethyl}cyclopropyl)piperidin-1-yl]pyrimidine;
5-chloro-2-[4-((1S,2R)-2-{2-[4-(methylsulfonyl)phenoxy]ethyl}cyclopropyl)piperidin-1-yl]pyrimidine;
5-chloro-2-[4-((1R,2S)-2-{2-[4-(methylsulfonyl)phenoxy]ethyl}cyclopropyl)piperidin-1-yl]pyrimidine;
rac cis-5-chloro-2-[4-(2-{2-[3-(methylsulfonyl)phenoxy]ethyl}cyclopropyl)piperidin-1-yl]pyrimidine; and
rac cis-5-chloro-2-[4-(2-{2-[3-(5-methyl-1,3,4-oxadiazol-2-yl)phenoxy]ethyl}cyclopropyl) piperidin-1-yl]pyrimidine; and pharmaceutically acceptable salts thereof.

Selective PPARγ modulators (SPPARγM's) that can be used in combination with the compounds of Formula I include, but are not limited to:
(2S)-2-({6-chloro-3-[6-(4-chlorophenoxy)-2-propylpyridin-3-yl]-1,2-benzisoxazol-5-yl}oxy)propanoic acid;
(2S)-2-({6-chloro-3-[6-(4-fluorophenoxy)-2-propylpyridin-3-yl]-1,2-benzisoxazol-5-yl}oxy)propanoic acid;
(2S)-2-{[6-chloro-3-(6-phenoxy-2-propylpyridin-3-yl)-1,2-benzisoxazol-5-yl]oxy}propanoic acid;
(2R)-2-({6-chloro-3-[6-(4-chlorophenoxy)-2-propylpyridin-3-yl]-1,2-benzisoxazol-5-yl}oxy)propanoic acid;
(2R)-2-{3-[3-(4-methoxy)benzoyl-2-methyl-6-(trifluoromethoxy)-1H-indol-1-yl]phenoxy}butanoic acid;
(2S)-2-{3-[3-(4-methoxy)benzoyl-2-methyl-6-(trifluoromethoxy)-1H-indol-1-yl]phenoxy}butanoic acid;
2-{3-[3-(4-methoxy)benzoyl-2-methyl-6-(trifluoromethoxy)-1H-indol-1-yl]phenoxy}-2-methylpropanoic acid; and
(2R)-2-{3-[3-(4-chloro)benzoyl-2-methyl-6-(trifluoromethoxy)-1H-indol-1-yl]phenoxy}propanoic acid; and pharmaceutically acceptable salts thereof.

Inhibitors of 11β-hydroxysteroid dehydrogenase type 1 that can be used in combination with the compounds of Formula I include, but are not limited to:
3-[1-(4-chlorophenyl)-trans-3-fluorocyclobutyl]-4,5-dicyclopropyl-r-4H-1,2,4-triazole;3-[1-(4-chlorophenyl)-trans-3-fluorocyclobutyl]-4-cyclopropyl-5-(1-methylcyclopropyl)-r-4H-1,2,4-triazole;
3-[1-(4-chlorophenyl)-trans-3-fluorocyclobutyl]-4-methyl-5-[2-(trifluoromethoxy)phenyl]-r-4H-1,2,4-triazole;
3-[1-(4-chlorophenyl)cyclobutyl]-4-methyl-5-[2-(trifluoromethyl)phenyl]-4H-1,2,4-triazole;
3-{4-[3-(ethylsulfonyl)propyl]bicyclo[2.2.2]oct-1-yl}-4-methyl-5-[2-(trifluoromethyl)phenyl]-4H-1,2,4-triazole;
4-methyl-3-{4-[4-(methylsulfonyl)phenyl]bicyclo[2.2.2]oct-1-yl}-5-[2-(trifluoromethyl)phenyl]-4H-1,2,4-triazole;
3-(4-{4-methyl-5-[2-(trifluoromethyl)phenyl]-4H-1,2,4-triazol-3-yl}bicyclo[2.2.2]oct-1-yl)-5-(3,3,3-trifluoropropyl)-1,2,4-oxadiazole;
3-(4-{4-methyl-5[2-(trifluoromethyl)phenyl]-4H-1,2,4-triazol-3-yl}bicyclo[2.2.2]oct-1-yl)-5-(3,3,3-trifluoroethyl)-1,2,4-oxadiazole;
5-(3,3-difluorocyclobutyl)-3-(4-{4-methyl-5-[2-(trifluoromethyl)phenyl]-4H-1,2,4-triazol-3-yl}bicyclo[2.2.2]oct-1-yl)-1,2,4-oxadiazole;
5-(1-fluoro-1-methylethyl)-3-(4-{4-methyl-5-[2-(trifluoromethyl)phenyl]-4H-1,2,4-triazol-3-yl}bicyclo[2.2.2]oct-1-yl)-1,2,4-oxadiazole;
2-(1,1-difluoroethyl)-5-(4-{4-methyl-5-[2-(trifluoromethyl)phenyl]-4H-1,2,4-triazol-3-yl}bicyclo[2.2.2]oct-1-yl)-1,3,4-oxadiazole;
2-(3,3-difluorocyclobutyl)-5-(4-{4-methyl-5-[2-(trifluoromethyl)phenyl]-4H-1,2,4-triazol-3-yl}bicyclo[2.2.2]oct-1-yl)-1,3,4-oxadiazole; and
5-(1,1-difluoroethyl)-3-(4-{4-methyl-5-[2-(trifluoromethyl)phenyl]-4H-1,2,4-triazol-3-yl}bicyclo[2.2.2]oct-1-yl)-1,2,4-oxadiazole; and pharmaceutically acceptable salts thereof.

Somatostatin subtype receptor 3 (SSTR3) antagonists that can be used in combination with the compounds of Formula I include, but are not limited to:

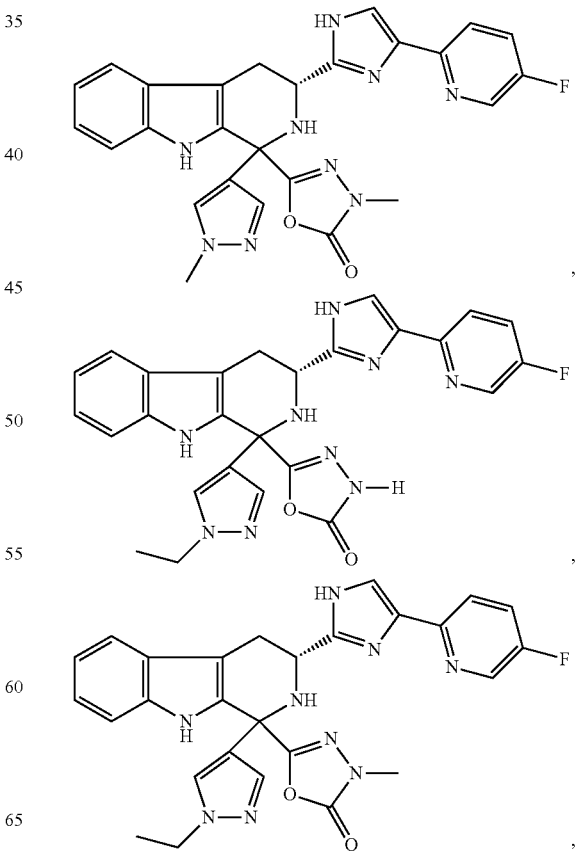

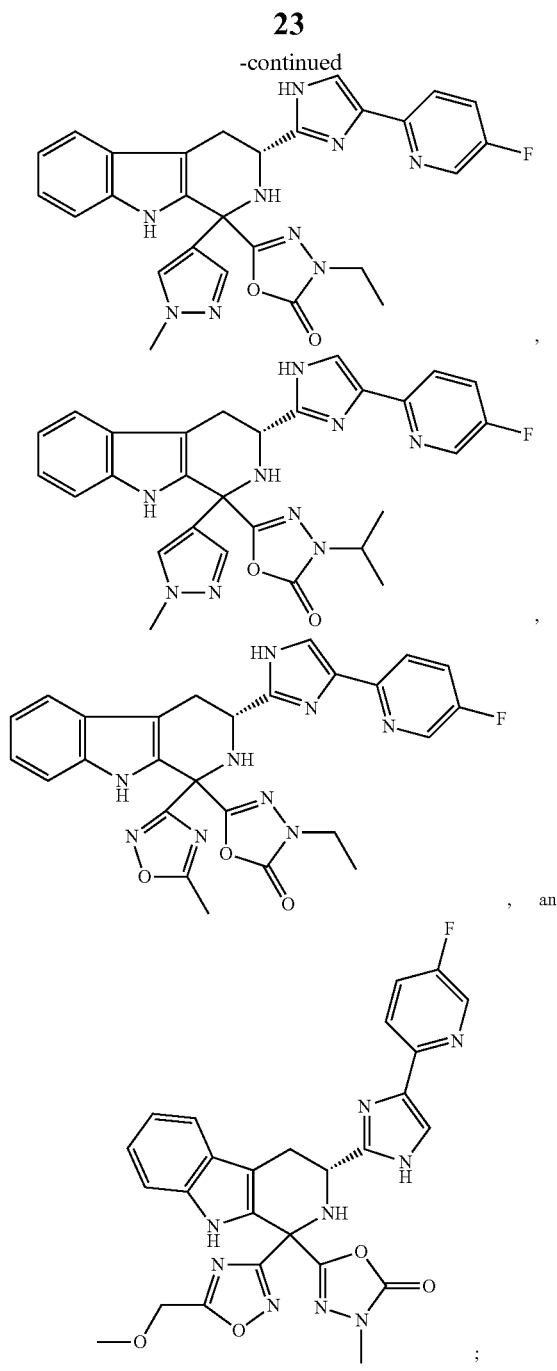
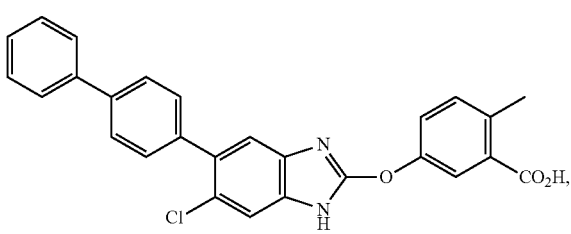
and pharmaceutically acceptable salts thereof.
AMP-activated Protein Kinase (AMPK) activators that can be used in combination with the compounds of Formula I include, but are not limited to:
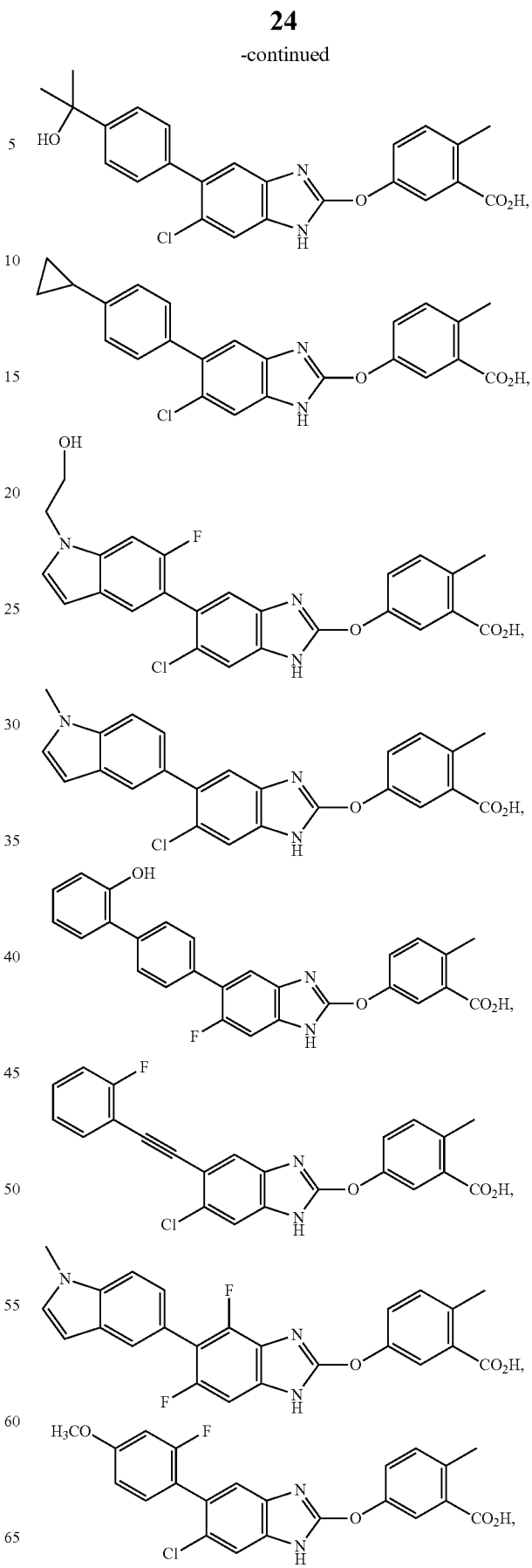

-continued

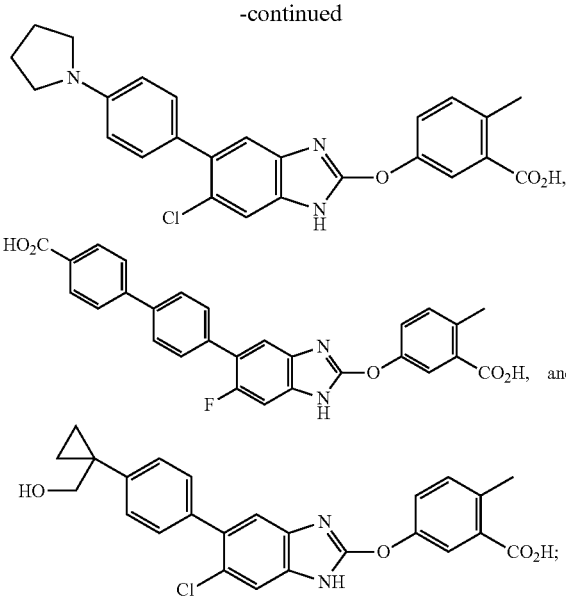

and phar
maceutically acceptable salts thereof.

Inhibitors of acetyl-CoA carboxylase-1 and 2 (ACC-1 and ACC-2) that can be used in combination with the compounds of Formula I include, but are not limited to:

3-{1'-[(1-cyclopropyl-4-methoxy-1H-indol-6-yl)carbonyl]-4-oxospiro[chroman-2,4'-piperidin]-6-yl}benzoic acid;
5-{1'-[(1-cyclopropyl-4-methoxy-1H-indol-6-yl)carbonyl]-4-oxospiro[chroman-2,4'-piperidin]-6-yl}nicotinic acid;
1'-[(1-cyclopropyl-4-methoxy-1H-indol-6-yl)carbonyl]-6-(1H-tetrazol-5-yl)spiro[chroman-2,4'-piperidin]-4-one;
1'-[(1-cyclopropyl-4-ethoxy-3-methyl-1H-indol-6-yl)carbonyl]-6-(1H-tetrazol-5-yl)spiro[chroman-2,4'-piperidin]-4-one; and
5-{1'-[(1-cyclopropyl-4-methoxy-3-methyl-1H-indol-6-yl)carbonyl]-4-oxo-spiro[chroman-2,4'-piperidin]-6-yl}nicotinic acid; and
pharmaceutically acceptable salts thereof.

In another aspect of the invention, a pharmaceutical composition is disclosed which comprises one or more of the following agents:
(a) a compound of structural Formula I;
(b) one or more compounds selected from the group consisting of:
(1) other dipeptidyl peptidase-IV (DPP-4) inhibitors;
(2) insulin sensitizers, including (i) PPARγ agonists, such as the glitazones (e.g. AMG 131, MBX2044, mitoglitazone, lobeglitazone, IDR-105, pioglitazone, rosiglitazone, and balaglitazone) and other PPAR ligands, including (1) PPARα/γ □dual agonists, such as ZYH1, YYH2, chiglitazar, GFT505, muraglitazar, aleglitazar, sodelglitazar, and naveglitazar, (2) PPARα agonists, such as fenofibric acid derivatives (e.g., gemfibrozil, clofibrate, ciprofibrate, fenofibrate and bezafibrate), (3) selective PPARγ modulators (SPPARγM's), and (4) PPARγ partial agonists; (ii) biguanides, such as metformin and its pharmaceutically acceptable salts, in particular, metformin hydrochloride, and extended-release formulations thereof, such as Glumetza®, Fortamet®, and GlucophageXR®; (iii) protein tyrosine phosphatase-1B (PTP-1B) inhibitors, such as ISI-113715, and TTP814;
(3) sulfonylurea and non-sulfonylurea insulin secretagogues, (e.g., tolbutamide, glyburide, glipizide, glimepiride, mitiglinide, and meglitinides, such as nateglinide and repaglinide);
(4) α-glucosidase inhibitors (e.g., acarbose, voglibose and miglitol);
(5) glucagon receptor antagonists;
(6) LDL cholesterol lowering agents such as (i) HMG-CoA reductase inhibitors (e.g., lovastatin, simvastatin, pravastatin, cerivastatin, fluvastatin, atorvastatin, pitavastatin, and rosuvastatin), (ii) bile acid sequestering agents (e.g., colestilan, cholestyramine, colestimide, colesevelam hydrochloride, colestipol, and dialkylaminoalkyl derivatives of a cross-linked dextran), (iii) inhibitors of cholesterol absorption, (e.g., ezetimibe), and (iv) acyl CoA:cholesterol acyltransferase inhibitors (e.g., avasimibe);
(7) HDL-raising drugs, such as niacin or a salt thereof and extended-release versions thereof; MK-524A, which is a combination of niacin extended-release and the DP-1 antagonist MK-524; and nicotinic acid receptor agonists;
(8) antiobesity compounds;
(9) agents intended for use in inflammatory conditions, such as aspirin, non-steroidal anti-inflammatory drugs (NSAIDs), glucocorticoids, and selective cyclooxygenase-2 (COX-2) inhibitors;
(10) antihypertensive agents, such as ACE inhibitors (e.g., enalapril, lisinopril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers (e.g., calcium channel blockers);
(11) glucokinase activators (GKAs) (e.g., AZD6370);
(12) inhibitors of 11β-hydroxysteroid dehydrogenase type 1 (e.g., such as those disclosed in U.S. Pat. No. 6,730,690; WO 03/104207; and WO 04/058741);
(13) inhibitors of cholesteryl ester transfer protein (CETP), (e.g., torcetrapib and MK-0859);
(14) inhibitors of fructose 1,6-bisphosphatase (e.g., such as those disclosed in U.S. Pat. Nos. 6,054,587; 6,110,903; 6,284,748; 6,399,782; and 6,489,476);
(15) inhibitors of acetyl CoA carboxylase-1 or 2 (ACC1 or ACC2);
(16) AMP-activated Protein Kinase (AMPK) activators;
(17) agonists of the G-protein-coupled receptors: (i) GPR-109, (ii) GPR-119 (e.g., MBX2982, and PSN821), and (iii) GPR-40 (e.g., TAK875, 5-[4-[[(1R)-4-[6-(3-hydroxy-3-methylbutoxy)-2-methylpyridine-3-yl]-2,3-dihydro-1H-indene-1-yl]oxy]phenyl]isothiazole-3-ol 1-oxide, 5-(4-((3-(2,6-dimethyl-4-(3-(methylsulfonyl)propoxy)phenyl)phenyl)methoxy)phenyl)iso, 5-(4-((3-(2-methyl-6-(3-hydroxypropoxy)pyridine-3-yl)-2-methylphenyl)methoxy)phenyl)isothiazole-3-ol 1-oxide, and 5-[4-[[3-[4-(3-aminopropoxy)-2,6-dimethylphenyl]phenyl]methoxy]phenyl]isothiazole-3-ol 1-oxide);
(18) SSTR3 antagonists (e.g., such as those disclosed in WO 2009/011836);
(19) neuromedin U receptor agonists (e.g., such as those disclosed in WO2009/042053, including, but not limited to, neuromedin S (NMS));
(20) inhibitors of stearoyl-coenzyme A delta-9 desaturase (SCD);
(21) GPR-105 antagonists (e.g., such as those disclosed in WO 2009/000087);
(22) inhibitors of glucose uptake, such as sodium-glucose transporter (SGLT) inhibitors and its various isoforms, such as SGLT-1; SGLT-2 (e.g., ASP1941, TS071, BI10773, tofogliflozin, LX4211, canagliflozin, dapagliflozin and remogliflozin; and SGLT-3);
(23) inhibitors of acyl coenzyme A:diacylglycerol acyltransferase 1 and 2 (DGAT-1 and DGAT-2);
(24) inhibitors of fatty acid synthase;

(25) inhibitors of acyl coenzyme A:monoacylglycerol acyltransferase 1 and 2 (MGAT-1 and MGAT-2);
(26) agonists of the TGR5 receptor (also known as GPBAR1, BG37, GPCR19, GPR131, and M-BAR);
(28) bromocriptine mesylate and rapid-release formulations thereof, and
(29) IL-1b antibodies (e.g., XOMA052, and canakinumab); and
(c) a pharmaceutically acceptable carrier.

When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl or n-propyl p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these.

Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require inhibition of dipeptidyl peptidase-IV enzyme activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Synthetic methods for preparing the compounds of the present invention are illustrated in the following Schemes and Examples. Starting materials are commercially available or may be made according to procedures known in the art or as illustrated herein.

The compounds of structural Formula I of the present invention can be prepared according to the procedures of the following Schemes and Examples, using appropriate materials and are further exemplified by the following specific examples. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogencarbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electron-spray ion-mass spectroscopy.

Synthetic methods for preparing the compounds of the present invention are illustrated in the following Schemes and Examples. Starting materials are commercially available or may be made according to procedures known in the art or as illustrated herein.

The compounds of the present invention can be prepared from intermediates such as those of Formula II and III using standard reductive amination conditions followed by deprotection,

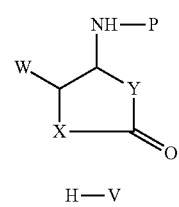

where P is a suitable nitrogen protecting group such as tert-butoxycarbonyl (BOC), benzyloxycarbonyl (Cbz), or 9-fluorenylmethoxycarbonyl (Fmoc). The preparation of these intermediates is described in the following Schemes.

SCHEME 1

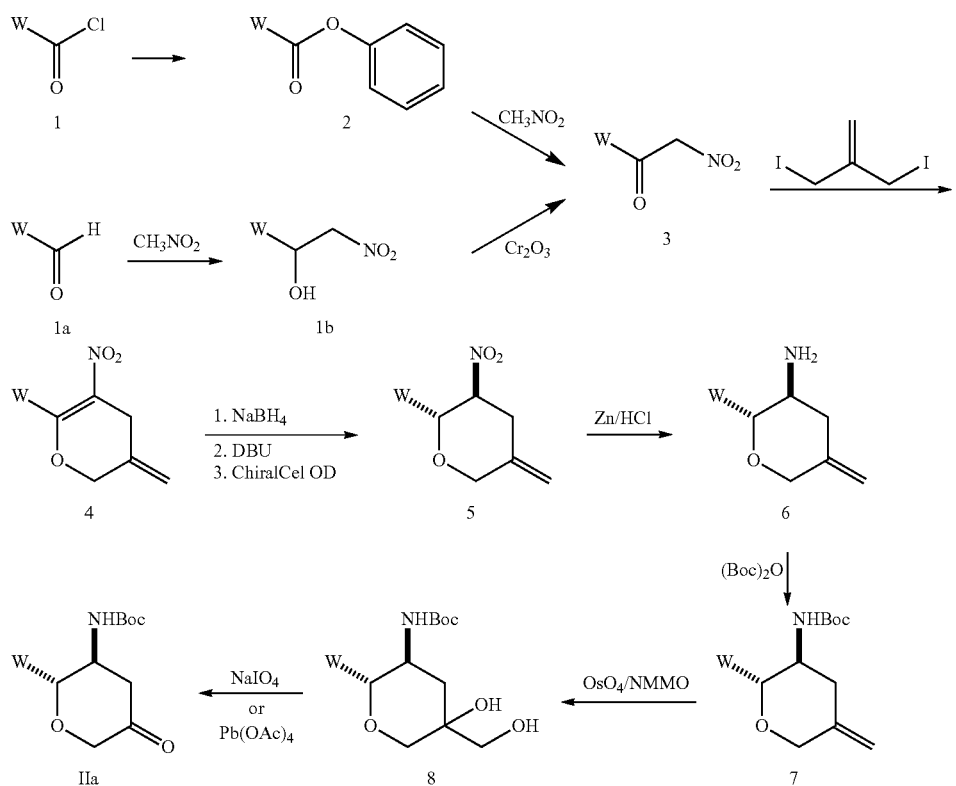

Intermediates of Formula II are known in the literature or may be conveniently prepared by a variety of methods familiar to those skilled in the art. One common route is illustrated in Scheme 1. Substituted benzoyl halide 1 is treated with phenol in the presence of a base such as N,N-diisopropylethylamine to form the ester 2. Treatment of 2 with the anion generated from nitromethane using sodium hydride gives the nitroketone 3. Alternatively, the nitroketone 3 can be made by reacting aldehyde 1a with nitromethane in the presence of a base and oxidizing the resulting nitroalcohol 1b with an oxidizing agent such as Jones reagent. Heating the nitroketone 3 with 3-iodo-2-(iodomethyl)prop-1-ene gives the pyran 4, which, when reduced with sodium borohydride and isomerized with a base such as 1,8-diazabicyclo[5.4.0]undec-7-ene (DBU), provides the trans pyran 5. The enantiomers of 5 may be separated at this stage by a variety of methods known to those skilled in the art. Conveniently, the racemate may be resolved by HPLC using a chiral column. The nitro-substituted pyran 5 is then reduced, for example, using zinc and an acid, such as hydrochloric acid, and the resulting amine 6 protected, for example, as its BOC derivative, by treatment with di-tert-butyl dicarbonate to give 7. Treatment of 7 with osmium tetroxide and N-methylmorpholine N-oxide forms the diol 8 which upon treatment with sodium periodate gives intermediate pyranone IIa.

SCHEME 2

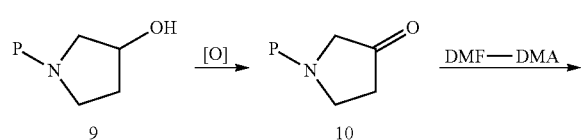

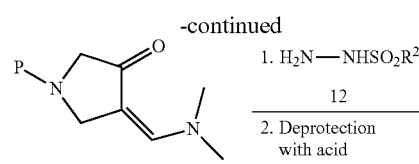

Intermediates of Formula III are known in the literature or may be conveniently prepared by a variety of methods familiar to those skilled in the art. One common route to prepare tetrahydropyrrolopyrazole IIIa is illustrated in Scheme 2. Protected pyrrolidinol 9 may be oxidized by a variety of methods, such as the Swern procedure, commonly known to those in the art, to give the ketone 10, which upon treatment and heating with N,N-dimethylformamide dimethyl acetal (DMF-DMA) gives 11. P represents the protecting group which can be Trityl- or Boc-protection. The desired intermediate IIIa may then be readily obtained by heating a solution of 11 with hydrazine 12 in a suitable solvent such as ethanol optionally in the presence of a base such as sodium ethoxide followed by removal of the protecting group with acid.

SCHEME 3

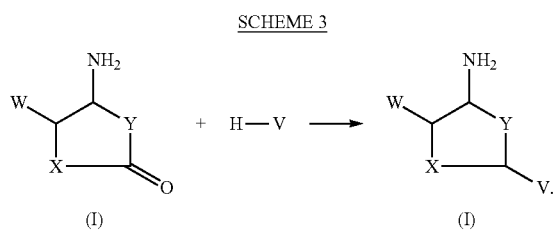

As illustrated in Scheme 3, the compounds of the present invention structural formula (I) may be prepared by reductive amination of Intermediate II in the presence of Intermediate III using reagents such as sodium cyanoborohydride, decaborane, or sodium triacetoxyborohydride in solvents such as dichloromethane, tetrahydrofuran, or methanol to provide Intermediate IV. The reaction is conducted optionally in the presence of a Lewis acid such as titanium tetrachloride or titanium tetraisopropoxide. The reaction may also be facilitated by adding an acid such as acetic acid. In some cases, Intermediate III may be a salt, such as a hydrochloric acid or trifluoroacetic acid salt, and in these cases it is convenient to add a base, generally N,N-diisopropylethylamine, to the reaction mixture. The protecting group is then removed with, for example, trifluoroacetic acid or methanolic hydrogen chloride in the case of Boc, or palladium-on-carbon and hydrogen gas in the case of Cbz to give the desired amine I. The product is purified, if necessary, by recrystallization, trituration, preparative thin layer chromatography, flash chromatography on silica gel, such as with a Biotage® apparatus, or HPLC. Compounds that are purified by HPLC may be isolated as the corresponding salt.

In some cases the product I or synthetic intermediates illustrated in the above schemes may be further modified, for example, by manipulation of substituents on W, Y or X. These manipulations may include, but are not limited to, reduction, oxidation, alkylation, acylation, and hydrolysis reactions that are commonly known to those skilled in the art. In some cases the order of carrying out the foregoing reaction schemes may be varied to facilitate the reaction or to avoid unwanted reaction products.

The compounds of structural Formula I of the present invention can be prepared according to the procedures of the following Schemes and Examples, using appropriate materials and are further exemplified by the following specific examples. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogencarbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electron-spray ion-mass spectroscopy.

The following is a list of abbreviations that may be useful when reading the description of the synthesis of the Intermediates and Examples shown below.

LIST OF ABBREVIATIONS

Alk=alkyl
Ar=aryl
Boc=tert-butoxycarbonyl
br broad
CH$_2$Cl$_2$=dichloromethane
d=doublet
DBU=1,8-diazabicyclo[5.4.0]undec-7-ene
DEAD=diethyl azodicarboxylate
DMA=N,N-dimethylacetamide
DMF=dimethylformamide
DMSO=dimethyl sulfoxide
ESI=electrospray ionization
EtOAc=ethyl acetate
HATU=O-(7-azabenzotriazol-1-yl)-N,N,N,N'-tetramethyluronium hexafluorophosphate
HOAc=acetic acid
LC-MS=liquid chromatography-mass spectroscopy
LiOH=lithium hydroxide
m=multiplet
MeOH=methyl alcohol
MgSO$_4$=magnesium sulfate
MS=mass spectroscopy
NaOH=sodium hydroxide
Na$_2$SO$_4$=sodium sulfate
NMR=nuclear magnetic resonance spectroscopy
PG=protecting group
Ph=phenyl
Rt or RT=room temperature
s=singlet
t=triplet
TFA=trifluoroacetic acid
THF=tetrahydrofuran

EXAMPLE 1

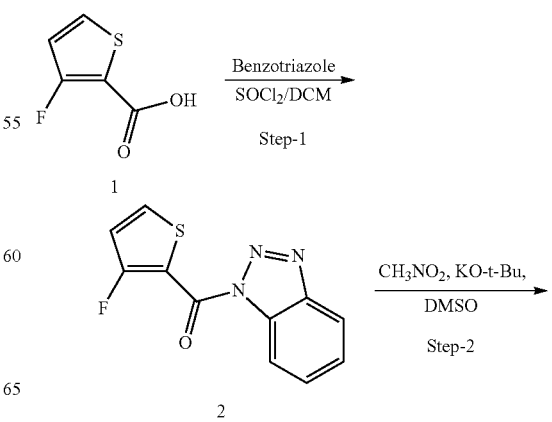

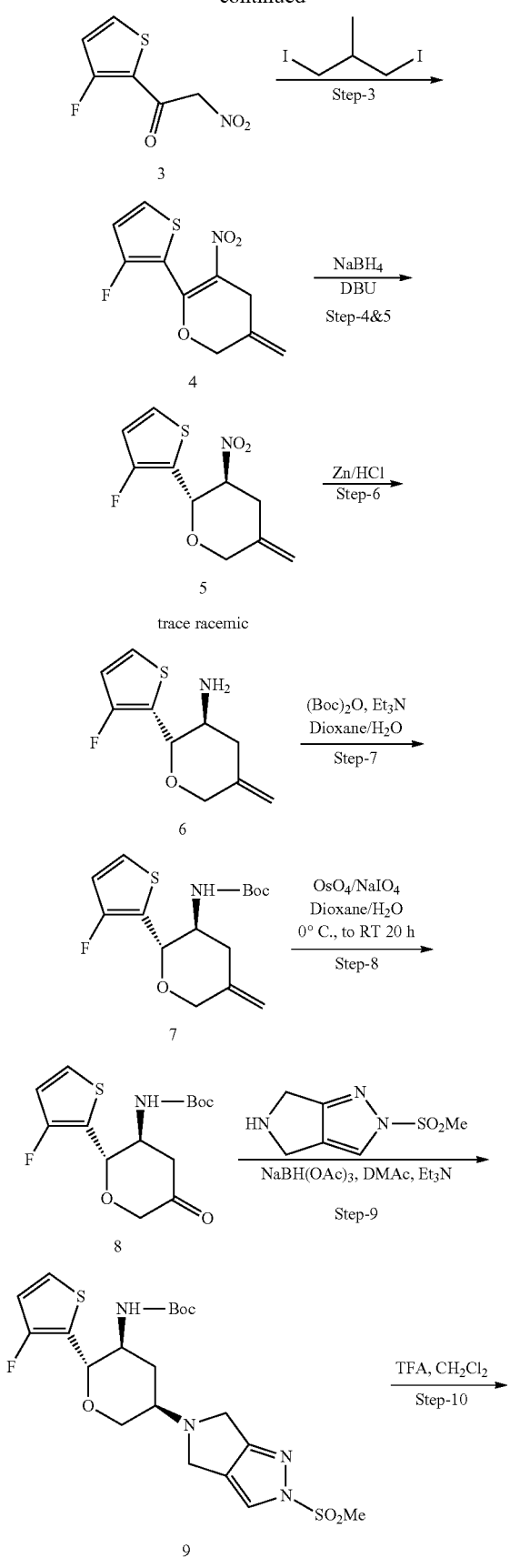

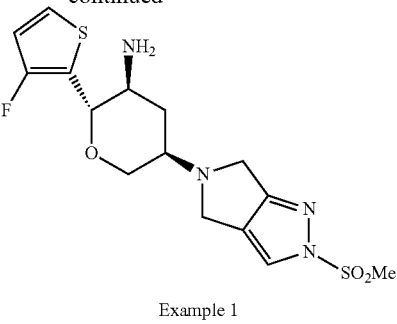

Example 1

Step 1. Preparation of Compound 2

To a solution of benzotriazole (Bt) (0.326 g, 2.73 mmol, 4 equiv) in anhydrous dichloromethane (2 mL), thionyl chloride (0.081 g, 0.69 mmol, 1 equiv) was added at room temperature with stirring. After 30 min, the carboxylic acid 1 (0.100 g, 0.69 mmol, 1 equiv) was added in one portion and stirring was continued for 2 h. The white precipitate was filtered off and washed with dichloromethane. The combined organic layers were washed with aqueous sodium hydroxide solution (2N, 3 mL), dried over anhydrous $Na_2SO_4$ and were concentrated. The crude compound 2 (150 mg) was taken to the next step without further purification.

$^1$H NMR (300 MHz, $CDCl_3$): δ 8.45-8.43 (m, 1H), 8.20-8.17 (m, 1H), 7.79-7.75 (m, 1H), 7.74-7.70 (m, 1H), 7.59-7.55 (m, 1H), 7.04 (d, J=5.48 Hz, 1H). Mol. formula $C_{11}H_6FN_3OS$, calcd. mol. wt. 247.25).

Step 2. Preparation of Compound 3

A mixture of nitromethane (0.037 g, 0.607 mmol, 1 equiv) and potassium tertbutoxide (0.15 g, 1.34 mmol, 2.2 equiv) in anhydrous dimethyl sulfoxide (2 mL) was stirred for 10 min at 10° C. The compound 2 (0.150 g, 0.607 mmol, 1 equiv) in anhydrous dimethyl sulfoxide (2 mL) was added dropwise. The resulting yellow suspension was stirred for 2 h at 10° C., and then for additional 6 h at room temperature. The mixture was poured into water, acidified with aq. 10% acetic acid, and then extracted with ethyl acetate. The organic layers separated were washed with water, dried over anhydrous $Na_2SO_4$ and concentrated. The residue was purified by flash chromatography (12-18% ethyl acetate in hexanes) to obtain compound 3 as yellow oil.

$^1$H NMR (400 MHz, $CDCl_3$): δ 7.75 (dd, J=3.88 Hz, J=5.88 Hz, 1H), 6.95 (d, J=5.48 Hz, 1H), 5.74 (d, J=1.32 Hz, 2H). Mol. formula $C_6H_4FNO_3S$, calcd. mol. wt. 189.16)

Step 3. Preparation of Compound 4

A mixture of 3-chloro-2-(chloromethyl) prop-1-ene (1.0 g, 8.06 mmol, 1 equiv) and sodium iodide (6.04 g, 40.34 mmol, 5 equiv) in anhydrous acetone (20 mL) was stirred at room temperature for 12 h. The solvent was removed under reduced pressure and the residue was dissolved in dichloromethane and water. The extracts were washed with water, dried over anhydrous $Na_2SO_4$ and concentrated to obtain 3-iodo-2-(iodomethyl)prop 1-ene as reddish oil.

To a solution of compound 3 (0.500 g, 2.77 mmol, 1 equiv) in anhydrous dimethyl formamide (3 mL), diisopropyl ethylamine (0.880 g, 6.92 mmol, 2.5 equiv) and iodo-2-(iodomethyl)prop 1-ene (1.27 g, 4.14 mmol, 1.5 equiv) were added and the mixture was heated to 60° C. for 3 h. The solvent was removed under reduced pressure and the crude was purified by flash chromatography (15-20% ethyl acetate in hexanes) to yield compound 4 as white solid.

$^1$H NMR (400 MHz, $CDCl_3$): δ 7.44 (dd, J=3.84 Hz, J=5.56 Hz, 1H), 6.82 (d, J=5.52 Hz, 1H), 5.34 (s, 1H), 5.26 (d,

J=0.76 Hz, 1H) 4.58 (s, 2H), 3.61(t, J=1.58 Hz, 2H). Mol. formula $C_{10}H_8FNO_3S$, calcd. mol. wt. 241.24).

Step 4 &5. Preparation of Compound 5

To a mixture of chloroform (60 mL) and isopropyl alcohol (12 mL) was added compound 4 (1.30 g, 5.39 mmol, 1 equiv) followed by silica gel (8.3 g) and sodium borohydride (0.815 g, 21.57 mmol, 4 equiv). The resulting pale yellow mixture stirred for 30 min at room temperature. The reaction mixture was quenched by the addition of hydrochloric acid (2N), filtered and then washed with ethyl acetate. The combined filtrate was washed with saturated sodium bicarbonate solution, brine and dried over anhydrous $Na_2SO_4$ and were concentrated. The resultant oil was dissolved in THF (10 mL) and 1,8-Diazabicyclo[5.4.0]undec-7-ene. (0.2 mL) was added. The resulting solution was stirred for 2 h and then quenched by the addition of hydrochloric acid (1N), and extracted with ethyl acetate. The organic layer separated was washed with water, dried over $Na_2SO_4$ and concentrated. The residue was purified by flash chromatography (15-20% ethyl acetate in hexanes) to obtain compound 5 as a colorless liquid.

$^1$H NMR (400 MHz, $CDCl_3$): δ 7.24 (dd, J=3.84 Hz, J=5.56 Hz, 1H), 6.76 (d, J=5.52 Hz, 1H), 5.18 (d, J=9.44 Hz, 1H), 5.10 (d, J=9.0 Hz, 2H),4.79-4.72 (m, 1H), 4.36 (d, J=12.68 Hz, 1H), 4.23 (d, J=12.72 Hz, 1H), 3.11-3.06 (m, 2H). Mol. formula $C_{10}H_{10}FNO_3S$, calcd. mol. wt. 243.25).

Step 6. Preparation of Compound 6

To a stirred solution of compound 5 (0.2 g, 0.822 mmol, 1 equiv) and zinc powder (0.537 g, 8.223 mmol, 10 equiv) in ethanol (7 mL) was added 6 N hydrochloric acid (3 mL) and stirred at room temperature for 1 h. The resulting mixture was filtered through celite bed, filtrate collected was concentrated. The crude compound 6 (200 mg) was taken to the next step without further purification.

Mol. formula $C_{10}H_{12}FNOS$, calcd. mol. wt. 213.27).

Step 7. Preparation of Compound 7

To a stirred solution of compound 6 (0.200 g, 0.938 mmol, 1 equiv) in dioxane:water (2:2 mL) triethylamine (0.270 g, 2.816 mmol, 3 equiv) was added at 0° C. followed by addition of Di-tert-butyl dicarbonate (0.2 g, 0.938 mmol, 1 equiv) dropwise and the reaction mixture was stirred for 3 h at room temperature. The reaction mixture was concentrated under reduced pressure, diluted with ethyl acetate, successively washed with water and brine solution. The organic layer was dried over anhydrous $Na_2SO_4$, concentrated under reduced pressure and purified by Isolera (5-8% ethyl acetate in hexanes) to obtain the desired product 7 as colorless liquid.

$^1$H NMR (400 MHz, $CDCl_3$): δ 7.17 (dd, J=3.92 Hz, J=5.52 Hz, 1H), 6.73 (d, J=5.48 Hz, 1H), 4.94 (d, J=9.68 Hz, 2H), 4.65-4.56 (m, 2H), 4.29 (d, J=12.48 Hz, 1H), 4.06 (d, J=12.52 Hz, 1H), 2.84 (dd, J=4.48 Hz, J=13.6 Hz, 1H),2.34-2.28 (m, 1H), 1.34 (s, 9H). Mol. formula $C_{15}H_{20}FNO_3S$, calcd. mol. wt. 313.39).

Step 8. Preparation of Compound 8

To a cooled solution of compound 8 (0.1 g, 0.319 mmol, 1.0 equiv) in dioxane: water (1+1 mL) sodium periodate (0.204 g, 0.958 mmol, 3.0 equiv) was added at 0° C. To this pale yellow mixture, osmium tetroxide (0.014 g 0.0063 mmol, 0.02 equiv) was added and the reaction mixture was stirred for 3 h at room temperature. The reaction mixture was concentrated under reduced pressure, diluted with ethyl acetate, successively washed with water and brine solution. The organic layer was dried over anhydrous $Na_2SO_4$, concentrated under reduced pressure and purified by Isolera (20-28% ethyl acetate in hexanes) to obtain the desired product 7 as white solid.

$^1$H NMR (400 MHz, $CDCl_3$): δ 7.24 (dd, J=3.92 Hz, J=5.52 Hz, 1H), 6.80 (d, J=5.56 Hz, 1H), 5.06 (br s, 1H), 4.76 (br s, 1H), 4.29-4.25 (m, 1H), 4.15-4.07 (m, 1H), 3.04 (dd, J=5.88 Hz, J=16.8 Hz, 1H), 2.87-2.80 (m, 1H), 1.38 (s, 9H). Mol. formula $C_{14}H_{18}FNO_4S$, calcd. mol. wt. 315.36).

Step 9. Preparation of Compound 9

To a mixture of amine (0.053 g, 0.152 mmol, 1.2 equiv) in dimethylacetamide (2 mL) was added triethylamine (0.038 g, 0.380 mmol, 3 equiv) and stirred for 10 min. Then compound 8 (0.040 g, 0.126 mmol, 1 equiv) and acetic acid (0.038 g, 0.634 mmol, 5 equiv) were added and the mixture was stirred for 30 min at room temperature. To the resulting solution, sodiumtriacetoxy borohydride (0.032 g, 0.152 mmol, 1.2 equiv) was added at 0° C. and allowed to stir at room temperature for 2 h. The mixture was poured into water and then extracted with ethyl acetate. The extracts were washed with water, dried over anhydrous $Na_2SO_4$ and concentrated. The residue was purified by flash chromatography (60-65% ethyl acetate in hexane) to obtain compound 9 as white solid.

$^1$H NMR (400 MHz, $CDCl_3$): δ 7.75 (s, 1H), 7.19 (dd, J=3.92 Hz, J=5.40 Hz, 1H), 6.74 (d, J=5.52 Hz, 1H), 4.57-4.49 (m, 2H), 4.27 (d, J=11.6 Hz, 1H), 3.96-3.80 (m, 5H), 3.31 (s, 3H), 2.54-2.50 (m, 1H), 1.34 (s, 9H). Mol. formula $C_{20}H_{27}FN_4O_5S_2$, calcd. mol. wt. 486.58).

Step 10. Preparation of Example 1

To a solution of compound 9 (0.040 g, 0.082 mmol, 1 equiv) in dichloromethane (2 mL) was added trifluoroacetic acid (1 mL) dropwise at 0° C. The resulting mixture was warmed to room temperature and stirred for 2 h. Reaction mixture was concentrated to dryness. The solid residue obtained was washed with diethyl ether and dried under vacuum to obtain trans-racemic Example 1 as di-TFA salt. Example 1 had an IC50 value of 90 nM.

$^1$H NMR (400 MHz, $CD_3OD$): δ 8.05 (s, 1H), 7.55 (dd, J=4.02 Hz, J=5.46 Hz, 1H), 6.94 (d, J=5.56 Hz, 1H), 4.72 (d, J=11.6 Hz, 1H), 4.54-4.43 (m, 5H), 3.80-3.75 (m, 2H), 3.61-3.55 (m, 1H), 3.43 (s, 3H), 2.79-2.77(m, 1H), 2.06-2.04(m, 1H). LC purity: 96.92%; ES/APCI-MS [M+H$^+$] m/z 387.2 (Mol. formula $C_{15}H_{19}FN_4O_3S_2$, calcd. mol. wt. 386.46). HPLC purity: 92.17%;

EXAMPLE 2

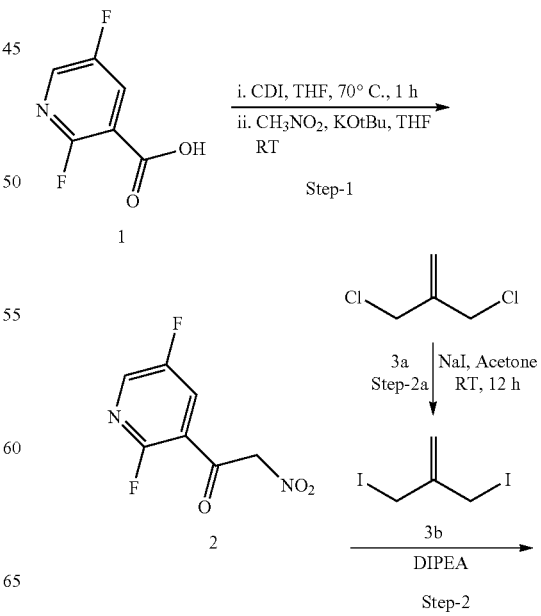

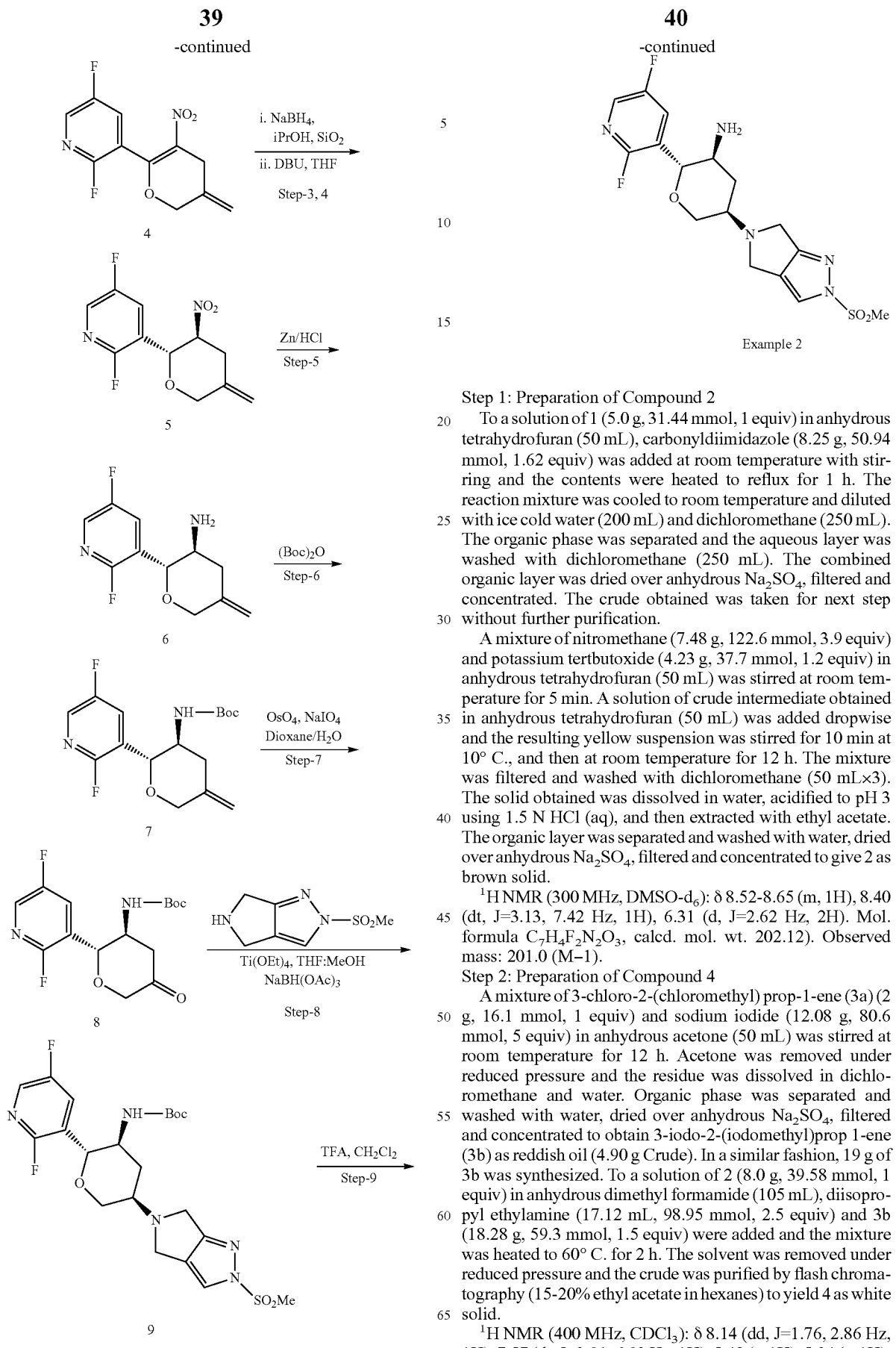

Example 2

Step 1: Preparation of Compound 2

To a solution of 1 (5.0 g, 31.44 mmol, 1 equiv) in anhydrous tetrahydrofuran (50 mL), carbonyldiimidazole (8.25 g, 50.94 mmol, 1.62 equiv) was added at room temperature with stirring and the contents were heated to reflux for 1 h. The reaction mixture was cooled to room temperature and diluted with ice cold water (200 mL) and dichloromethane (250 mL). The organic phase was separated and the aqueous layer was washed with dichloromethane (250 mL). The combined organic layer was dried over anhydrous $Na_2SO_4$, filtered and concentrated. The crude obtained was taken for next step without further purification.

A mixture of nitromethane (7.48 g, 122.6 mmol, 3.9 equiv) and potassium tertbutoxide (4.23 g, 37.7 mmol, 1.2 equiv) in anhydrous tetrahydrofuran (50 mL) was stirred at room temperature for 5 min. A solution of crude intermediate obtained in anhydrous tetrahydrofuran (50 mL) was added dropwise and the resulting yellow suspension was stirred for 10 min at 10° C., and then at room temperature for 12 h. The mixture was filtered and washed with dichloromethane (50 mL×3). The solid obtained was dissolved in water, acidified to pH 3 using 1.5 N HCl (aq), and then extracted with ethyl acetate. The organic layer was separated and washed with water, dried over anhydrous $Na_2SO_4$, filtered and concentrated to give 2 as brown solid.

$^1$H NMR (300 MHz, DMSO-$d_6$): δ 8.52-8.65 (m, 1H), 8.40 (dt, J=3.13, 7.42 Hz, 1H), 6.31 (d, J=2.62 Hz, 2H). Mol. formula $C_7H_4F_2N_2O_3$, calcd. mol. wt. 202.12). Observed mass: 201.0 (M−1).

Step 2: Preparation of Compound 4

A mixture of 3-chloro-2-(chloromethyl) prop-1-ene (3a) (2 g, 16.1 mmol, 1 equiv) and sodium iodide (12.08 g, 80.6 mmol, 5 equiv) in anhydrous acetone (50 mL) was stirred at room temperature for 12 h. Acetone was removed under reduced pressure and the residue was dissolved in dichloromethane and water. Organic phase was separated and washed with water, dried over anhydrous $Na_2SO_4$, filtered and concentrated to obtain 3-iodo-2-(iodomethyl)prop 1-ene (3b) as reddish oil (4.90 g Crude). In a similar fashion, 19 g of 3b was synthesized. To a solution of 2 (8.0 g, 39.58 mmol, 1 equiv) in anhydrous dimethyl formamide (105 mL), diisopropyl ethylamine (17.12 mL, 98.95 mmol, 2.5 equiv) and 3b (18.28 g, 59.3 mmol, 1.5 equiv) were added and the mixture was heated to 60° C. for 2 h. The solvent was removed under reduced pressure and the crude was purified by flash chromatography (15-20% ethyl acetate in hexanes) to yield 4 as white solid.

$^1$H NMR (400 MHz, CDCl$_3$): δ 8.14 (dd, J=1.76, 2.86 Hz, 1H), 7.57 (dt, J=3.01, 6.93 Hz, 1H), 5.42 (s, 1H), 5.34 (s, 1H), 4.66 (s, 2H), 3.63 (s, 2H) Mol. formula $C_{11}H_8F_2N_2O_3$, calcd. mol. wt. 254.19). Observed mass: 255.2 (M+H$^+$).

Steps 3 and 4: Preparation of Compound 5

To a mixture of chloroform (86 mL) and isopropyl alcohol (17.4 mL) was added 4 (2.0 g, 7.86 mmol, 1 equiv) followed by silica gel (60-120 mesh size, 12 g) and sodium borohydride (1.19 g, 31.47 mmol, 4 equiv). The resulting pale yellow mixture stirred for 2 h at room temperature. The reaction mixture was quenched by the addition of hydrochloric acid (1.5 N), filtered and washed with ethyl acetate. The combined filtrate was washed with saturated sodium bicarbonate solution, brine and dried over anhydrous $Na_2SO_4$, filtered and concentrated. The resultant oil was dissolved in THF (40 mL) and 1,8-diazabicyclo[5.4.0]undec-7-ene (0.084 mL) was added. The resulting solution was stirred for 2 h at room temperature. The solvent was removed under reduced pressure and the crude was purified by flash chromatography (15-20% ethyl acetate in hexanes) to yield racemic trans 5* and the racemic cis 5a* as colorless oils.

*(Based on 2D NMR)

5

$^1$H NMR (400 MHz, CDCl$_3$): δ 8.06 (dd, J=1.60, 2.93 Hz, 1H), 7.62 (dt, J=2.93, 7.07 Hz, 1H), 5.15 (s, 1H), 5.13 (s, 1H), 5.00 (d, J=9.60 Hz, 1H), 4.73 (dt, J=6.27, 9.80 Hz, 1H), 4.39 (d, J=12.80 Hz, 1H), 4.23 (d, J=12.80 Hz, 1H), 3.09-3.18 (m, 2H). Mol. formula $C_{11}H_{10}F_2N_2O_3$, calcd. mol. wt. 256.21). Observed mass: 257.2 (M+H$^+$).

5a $^1$H NMR (400 MHz, CDCl$_3$): δ 7.99 (t, J=2.13 Hz, 1H), 7.67 (dt, J=3.20, 7.47 Hz, 1H), 5.08-5.18 (m, 3H), 4.99 (s, 1H), 4.61 (d, J=12.80 Hz, 1H), 4.32 (d, J=12.80 Hz, 1H), 3.16 (d, J=15.74 Hz, 1H), 2.86-2.99 (m, 1H). Mol. formula $C_{11}H_{10}F_2N_2O_3$, calcd. mol. wt. 256.21). Observed mass: 257.2 (M+H$^+$).

Steps 5 and 6: Preparation of Compound 7

To a stirred solution of 5 (648 mg, 2.5 mmol, 1 equiv) and zinc powder (1.65 g, 25.29 mmol, 10 equiv) in ethanol (20 mL) was added 6 N hydrochloric acid (9.29 mL) and stirred at room temperature for 1 h. The resulting mixture was filtered through celite bed, and the filtrate was concentrated. The crude 6 (572 mg) was taken to the next step without further purification.

To a stirred solution of 6 (572 mg, 2.5 mmol, 1 equiv) in dioxane:water (10 mL+10 mL), triethylamine (1.0 mL, 7.5 mmol, 3 equiv) was added at 0° C. followed by addition of di-tert-butyl dicarbonate (551 mg, 2.5 mmol, 1 equiv) dropwise and the reaction mixture was stirred at room temperature for 3 h. The reaction mixture was concentrated under reduced pressure, diluted with ethyl acetate, successively washed with water and brine solution. The organic layer was dried over anhydrous $Na_2SO_4$, filtered and concentrated under reduced pressure. The crude obtained was purified by Isolera (5-8% ethyl acetate in hexanes) to obtain 7 (633 mg, 76.7%) as white solid.

$^1$H NMR (300 MHz, CDCl$_3$): δ 7.94 (br. s., 1H), 7.68-7.78 (m, 1H), 4.99 (s, 1H), 4.96 (s, 1H), 4.53 (d, J=9.33 Hz, 1H), 4.40 (d, J=9.70 Hz, 1H), 4.32 (dd, J=1.46, 12.62 Hz, 1H), 4.07 (d, J=12.62 Hz, 1H), 3.62-3.77 (m, 1H), 2.82 (ddd, J=1.46, 4.62, 13.31 Hz, 1H), 2.29 (t, J=12.44 Hz, 1H), 1.27 (s, 9H) Mol. formula $C_{16}H_{20}F_2N_2O_3$, calcd. mol. wt. 326.34). Observed mass: 227.2 (M-Boc).

Step 7: Preparation of Compound 8

To a cooled solution of compound 7 (500 mg, 1.53 mmol, 1.0 equiv) in dioxane: water (15+10 mL) sodium periodate (982 mg, 4.5 mmol, 3.0 equiv) was added at 0° C. To this pale yellow mixture, osmium tetroxide (7.7 mg, 0.03 mmol, 0.02 equiv) was added and the reaction mixture was stirred at room temperature for 3 h. The reaction mixture was concentrated under reduced pressure, diluted with ethyl acetate, successively washed with water and brine solution. The organic layer was dried over anhydrous $Na_2SO_4$, filtered and concentrated under reduced pressure. The crude obtained was purified by Isolera (20-28% ethyl acetate in hexanes) to obtain 8 as white solid.

$^1$H NMR (400 MHz, CDCl$_3$): δ 8.01 (br. s., 1H), 7.67-7.80 (m, 1H), 4.76 (d, J=9.07 Hz, 1H), 4.59-4.69 (m, 1H), 4.28-4.37 (m, 1H), 4.14 (d, J=16.27 Hz, 1H), 4.03-4.11 (m, 1H), 3.06 (dd, J=5.60, 16.54 Hz, 1H), 2.68 (dd, J=11.20, 16.27 Hz, 1H), 1.31 (s, 9H). Mol. formula $C_{15}H_{18}F_2N_2O_4$, calcd. mol. wt. 328.31). Observed mass: 327.2 (M−1).

Step 8: Synthesis of Compound 9

To a solution of amine (0.526 g, 1.52 mmol, 2.5 equiv) in methanol:tetrahydrofuran (3 mL:5 mL) was added triethylamine (0.254 mL, 1.8 mmol, 3 equiv) and stirred for 10 min. To this, 8 (0.200 g, 0.6 mmol, 1 equiv) was added followed by titaniumtetraethoxide (0.306 mL, 1.46 mmol, 2.4 equiv) and the mixture was stirred for 12 h at room temperature. The reaction mixture was concentrated and diluted with methanol (10 mL). Sodium triacetoxyborohydride (0.308 g, 1.46 mmol, 2.4 equiv) was added at 0° C. and the mixture was stirred at room temperature for 3 h and concentrated. The reaction mixture was neutralized with aqueous ammonia (3 mL) and then extracted with ethyl acetate. The extracts were washed with water, dried over anhydrous $Na_2SO_4$, filtered and concentrated. The residue obtained was purified by flash chromatography (70-80% ethyl acetate in hexane) to obtain 9 as white solid.

Mol. formula $C_{21}H_{27}F_2N_5O_5S$, calcd. mol. wt. 499.53. Observed mass: 500.3 (M+1).

Step 9: Synthesis of Example 2

To a solution of 9 (0.030 g, 0.060 mmol, 1 equiv) in dichloromethane (2 mL) was added trifluoroacetic acid (0.4 mL) dropwise at 0° C. The resulting mixture was warmed to room temperature and stirred for 2 h. The reaction mixture was concentrated to dryness. The solid residue obtained was purified by reverse phase preparative HPLC to give two fractions of Example 2 as triple TFA salt (7 mg, 94% pure and 6 mg, 86% pure, 29%) as colorless solids. Example 2 had an IC$_{50}$ of 100 nM.

$^1$H NMR (400 MHz, CD$_3$OD): δ 8.21 (dd, J=1.88, 2.89 Hz, 1H), 8.03 (s, 1H), 7.96 (dt, J=3.01, 7.40 Hz, 1H), 4.67 (d, J=10.04 Hz, 1H), 4.46-4.52 (m, 1H), 4.29-4.44 (m, 4H), 3.61-3.74 (m, 3H), 3.43 (s, 3H), 2.73-2.82 (m, 1H), 2.01 (q, J=11.63 Hz, 1H). Mol. formula $C_{16}H_{19}F_2N_5O_3S$, calcd. mol. wt. 399.42). Observed mass: 400.2 (M+1).

Example of a Pharmaceutical Formulation

As a specific embodiment of an oral pharmaceutical composition, a 100 mg potency tablet is composed of 100 mg of any one of the Examples, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A compound of structural Formula I:

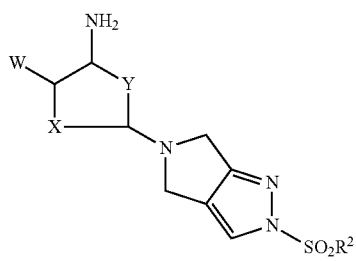
(I)

or a pharmaceutically acceptable salt thereof; wherein
W is selected from the group consisting of 2-thienyl, 3-thienyl, 2-furanyl, 3-furanyl, benzothiophenyl, pyridazine and pyridyl wherein W is unsubstituted or substituted independently with one to five $R^1$ substituents;
each R1 is independently selected from the group consisting of:
halogen,
cyano,
hydroxy,
$C_{1-6}$ alkyl, optionally substituted with one to five fluorines, and
$C_{1-6}$ alkoxy, optionally substituted with one to five fluorines;
$R^2$ is selected from the group consisting of
$C_{1-10}$ alkyl, wherein alkyl is optionally substituted with one to five substituents independently selected from fluorine and hydroxy,
$(CH_2)_m$—$C_{3-6}$ cycloalkyl, wherein cycloalkyl is optionally substituted with one to three substituents independently selected from halogen, hydroxy, cyano, nitro, $CO_2H$, $C_{1-6}$ alkyloxycarbonyl, $C_{1-6}$ alkyl, and $C_{1-6}$ alkoxy, wherein alkyl and alkoxy are optionally substituted with one to five fluorines,
X and Y are each independently selected from the group consisting of $(CH_2)_n$ and $(CH_2)_m$—O—$(CH_2)_m$;
n is selected from the group consisting of 1, 2 and 3; and
m is selected from the group consisting of 0, 1, 2, and 3.

2. The compound of claim 1 wherein $R^1$ is independently selected from the group consisting of fluorine, chlorine, bromine, methyl, trifluoromethyl, and trifluoromethoxy.

3. The compound of claim 1 wherein X is —$CH_2CH_2$—.

4. The compound of claim 1 wherein X is —$OCH_2$— or —$OCH_2CH_2$—.

5. The compound of claim 1 wherein Y is —$CH_2$—.

6. The compound of claim 1 wherein $R^2$ is selected from the group consisting of —$C_{1-6}$ alkyl, and —$C_{3-6}$ cycloalkyl.

7. The compound of claim 6 wherein $R^2$ is —$C_{1-6}$ alkyl or —$C_{3-6}$ cycloalkyl, wherein alkyl and cycloalkyl are optionally substituted with one to five fluorines.

8. The compound of claim 1 of structural Formula Ia or Ib having the indicated stereochemical configuration at the two stereogenic carbon atoms marked with an *:

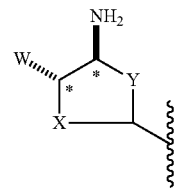
(Ia)

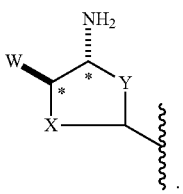
(Ib)

9. The compound of claim 8 of structural Formula Ia having the indicated absolute stereochemical configuration at the two stereogenic carbon atoms marked with an *:

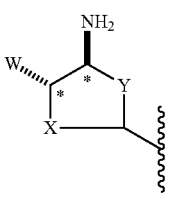
(Ia)

10. The compound of claim 1 of structural formulae Ic or Id having the indicated stereochemical configuration at the three stereogenic carbon atoms marked with an *:

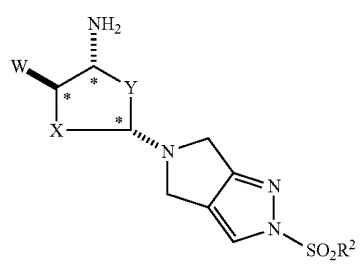
I(c)

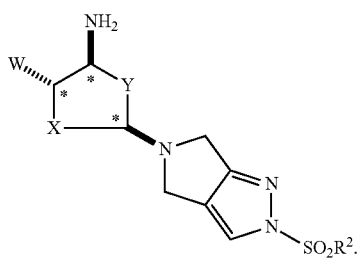
I(d)

11. The compound of claim 10 of structural Formula Id having the indicated absolute stereochemical configuration at the three stereogenic carbon atoms marked with an *:

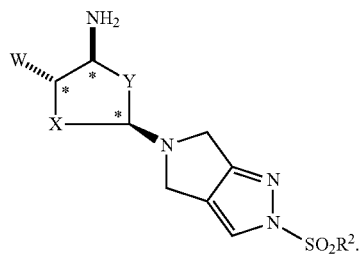

I(d)

12. A compound which is selected from the group consisting of:

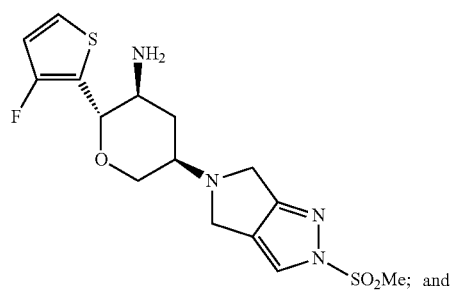

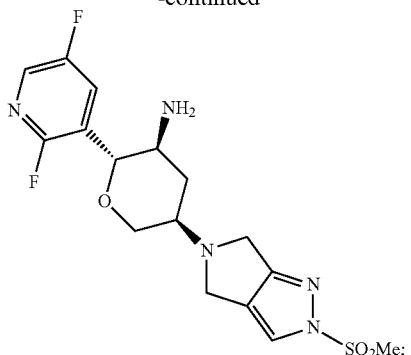

or a pharmaceutically acceptable salt thereof.

13. A pharmaceutical composition which comprises a compound of claim 1 and a pharmaceutically acceptable carrier.

14. The pharmaceutical composition of claim 13 additionally comprising metformin.

15. A method for treating non-insulin dependent (Type 2) diabetes in a mammal in need thereof comprising administering to the mammal a therapeutically effective amount of a compound of claim 1.

* * * * *